(12) United States Patent
Kotake et al.

(10) Patent No.: US 7,910,734 B2
(45) Date of Patent: *Mar. 22, 2011

(54) CRYSTAL AND SALT OF 1-CYCLOPROPYLMETHYL-4-[2-(3,3,5,5-TETRAMETHYLCYCLOHEXYL)PHENYL] PIPERAZINE

(75) Inventors: Makoto Kotake, Tsukuba (JP); Naoki Yoneda, Tsukuba (JP); Katsunobu Osada, Kakamigahara (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 229 days.

This patent is subject to a terminal disclaimer.

(21) Appl. No.: 11/793,374

(22) PCT Filed: Dec. 16, 2005

(86) PCT No.: PCT/JP2005/023166

§ 371 (c)(1),
(2), (4) Date: Nov. 28, 2007

(87) PCT Pub. No.: WO2006/068058

PCT Pub. Date: Jun. 29, 2006

(65) Prior Publication Data

US 2008/0161566 A1    Jul. 3, 2008

(30) Foreign Application Priority Data

Dec. 20, 2004  (JP) ................. 2004-368315
May 25, 2005   (JP) ................. 2005-151697

(51) Int. Cl.
  *C07D 295/00*       (2006.01)
(52) U.S. Cl. ................. 544/392; 544/395
(58) Field of Classification Search .......... 544/392, 544/395
  See application file for complete search history.

(56) References Cited

U.S. PATENT DOCUMENTS

| | | | |
|---|---|---|---|
| 5,244,901 A | 9/1993 | George et al. | |
| 2004/0092507 A1 | 5/2004 | Biggers et al. | |
| 2005/0261291 A1 * | 11/2005 | Kawahara et al. | 514/235.5 |

FOREIGN PATENT DOCUMENTS

| | | |
|---|---|---|
| EP | 0748800 A2 | 12/1996 |
| EP | 1 698 620 A1 | 9/2006 |
| EP | 1 832 580 A1 | 9/2007 |
| JP | 5-186434 A | 7/1993 |
| JP | 2003-506377 A | 2/2003 |
| JP | 2003-192673 A | 7/2003 |
| JP | 2004-523529 A | 8/2004 |
| WO | WO-93/11117 A1 | 6/1993 |
| WO | WO-01/09138 A2 | 2/2001 |
| WO | WO-02/18320 A2 | 3/2002 |
| WO | WO-02/059108 A1 | 8/2002 |
| WO | WO-03/033466 A1 | 4/2003 |
| WO | WO-03/089410 A1 | 10/2003 |
| WO | WO-2005/005382 A2 | 1/2005 |
| WO | WO 2005/063705 * | 7/2005 |
| WO | WO-2005/063705 A1 | 7/2005 |

OTHER PUBLICATIONS

Cowart et al., "Discovery of 2-(4-Pyridin-2-yl piperazin-1-ylmethyl)-1H-benzimidazole (ABT-724), a Dopaminergic Agent with a Novel Mode of Action for the Potential Treatment of Erectile Disfunction," Journal of Medicinal Chemistry, vol. 47, No. 15, 2004, pp. 3853-3864.
Podolsky et al., "Inflammatory Bowel Disease," N. Engl. J. Med., vol. 347, No. 6, 2002, pp. 417-429.
Ghosh et al., "Natalizumab for active Crohn's disease," N. Engl. J. Med., vol. 348, No. 1, 2003, pp. 24-32.
Shimoyama et al., "Granulocyte adsorption therapy in active period of ulcerative colitis," Japanese Journal of Apheresis, vol. 18, No. 1, 1999, pp. 117-131.
Sweeney et al., "Rheumatoid arthritis," Int. J. Biochem. Cell. Biol., vol. 36, 2004. pp. 372-378.
Lebwohl, "Psoriasis," Lancet Neurology, vol. 361, 2003, pp. 1197-1204.
Polman et al., "New and emerging treatment options for multiple sclerosis," Lancet Neurology, vol. 2, 2003, pp. 563-566.
Rosenwasser, "The role of T lymphocytes in the pathogenesis of asthma," J. Allergy Clin. Immunol., vol. 111, No. 3, 2003, pp. 450-463.
Schon et al., "The molecular basis of lymphocyte recruitment to the skin," J. Invest. Dermatol., vol. 121, No. 5, 2003, pp. 951-962.
Barbara et al., "A role for inflammation in irritable bowel syndrome," Gut., vol. 51, Suppl. 1, 2002, pp. 41-44.
Fleming, Ian et al., "Two New Oxindole Syntheses[†]" Journal of the Chemical Society, Perkin Transactions 1, 1986, pp. 349-359.
Communication mailed Oct. 5, 2009 in corresponding European application No. 06746829.8.

* cited by examiner

*Primary Examiner* — James O Wilson
*Assistant Examiner* — Erich A Leeser
(74) *Attorney, Agent, or Firm* — Birch, Stewart, Kolasch & Birch, LLP

(57) ABSTRACT

Salts and crystals of 1-cyclopropylmethyl-4-[2-(3,3,5,5-tetramethylcyclohexyl)phenyl]piperazine have excellent cell adhesion inhibitory action and cell infiltration inhibitory action, and are useful as therapeutic or prophylactic agents for various inflammatory diseases and autoimmune diseases associated with adhesion and infiltration of leukocytes, such as inflammatory bowel disease (particularly ulcerative colitis or Crohn's disease), irritable bowel syndrome, rheumatoid arthritis, psoriasis, multiple sclerosis, asthma and atopic dermatitis.

13 Claims, 14 Drawing Sheets

CRYSTAL AND SALT OF 1-CYCLOPROPYLMETHYL-4-[2-(3,3,5,5-TETRAMETHYLCYCLOHEXYL)PHENYL]PIPERAZINE

TECHNICAL FIELD

The present invention relates to salts and crystals of 1-cyclopropylmethyl-4-[2-(3,3,5,5-tetramethylcyclohexyl)phenyl]piperazine which are useful as cell adhesion inhibitors or cell infiltration inhibitors. Theses compounds are particularly useful as therapeutic or prophylactic agents for various diseases associated with adhesion and infiltration of leukocyte, such as inflammatory bowel disease (particularly ulcerative colitis or Crohn's disease), irritable bowel syndrome, rheumatoid arthritis, psoriasis, multiple sclerosis, asthma and atopic dermatitis.

BACKGROUND ART

Inflammatory reaction is accompanied by infiltration of leukocytes, typically neutrophils and lymphocytes, into inflammatory sites. Infiltration of leukocytes is defined as migration of leukocytes such as neutrophils and lymphocytes out of vessels and into the surrounding tissues as a consequence of initiation and activation by cytokines, chemokines, lipids and complement to interact called "rolling" or "tethering" with vascular endothelial cells activated by cytokines such as IL-1 or TNFα, followed by adhesion to the vascular endothelial cells.

As explained below, relationship between leukocyte adhesion or infiltration and various inflammatory diseases and autoimmune diseases was reported. Such reports have raised the possibility that compounds having cell adhesion inhibitory action or cell infiltration inhibitory action may serve as therapeutic or prophylactic agents for such diseases.

(1) Therapeutic or prophylactic agents for inflammatory bowel disease (ulcerative colitis, Crohn's disease and the like) (see Non-patent documents 1, 2 and 3)
(2) Therapeutic or prophylactic agents for rheumatoid arthritis (see Non-patent document 4)
(3) Therapeutic or prophylactic agents for psoriasis (see Non-patent document 5)
(4) Therapeutic or prophylactic agents for multiple sclerosis (see Non-patent document 6)
(5) Therapeutic or prophylactic agents for asthma (see Non-patent document 7)
(6) Therapeutic or prophylactic agents for atopic dermatitis (see Non-patent document 8)
(7) Therapeutic or prophylactic agents for irritable bowel syndrome (see Non-patent document 9)

Thus, substances which inhibit cell adhesion or cell infiltration are expected to be useful as therapeutic or prophylactic agents for various inflammatory diseases and autoimmune diseases associated with adhesion and infiltration of leukocytes, such as inflammatory bowel disease (particularly ulcerative colitis or Crohn's disease), irritable bowel syndrome, rheumatoid arthritis, psoriasis, multiple sclerosis, asthma and atopic dermatitis.

Compounds are also known which have anti-inflammatory action based on inhibition of adhesion of leukocyte and vascular endothelial cell, or anti-inflammatory action based on inhibition of leukocyte infiltration (these will hereinafter be referred to as cell adhesion inhibitors and cell infiltration inhibitors, respectively), such as the following compound (see Patent document 1).

[Chemical Formula 1]

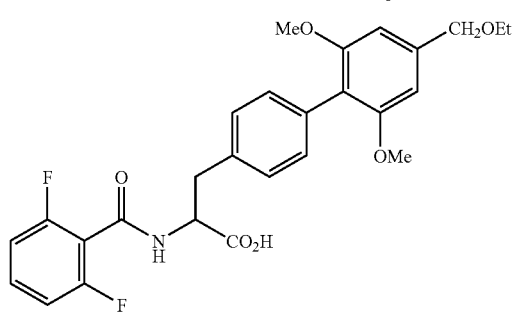

However, 1-cyclopropylmethyl-4-[2-(3,3,5,5-tetramethylcyclohexyl)phenyl]piperazine according to the present invention (the chemical formula is represented by the following formula (I)) is characterized by including a partial chemical structure having piperazine at the ortho position of a benzene ring bonded to cyclohexyl group, therefore differ in their structures from the aforementioned cell adhesion inhibitors or cell infiltration inhibitors.

[Chemical Formula 2]

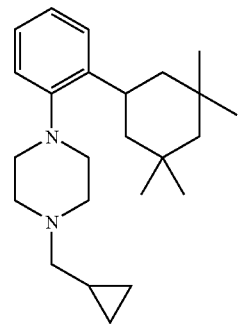

(I)

The known compound comprising a partial chemical structure having piperazine at the ortho position of a benzene ring bonded to cyclohexyl group, as a chemical structural feature of the compounds according to the present invention, is the compound represented by the following formula (see Patent document 2).

[Chemical Formula 3]

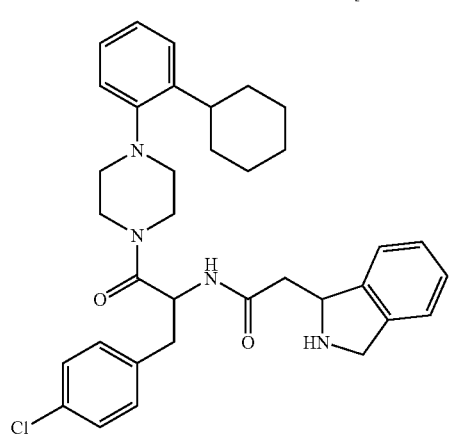

However, the patent application discloses only its use as an anti-obesity agent and diabetes treatment based on the melanocortin receptor agonistic activity of the compound, while it neither discloses nor suggests its use as an anti-inflammatory agent based on inhibitory action of leukocyte adhesion or infiltration.

Other than the above compounds, the compound represented by the following formula is known (see Non-patent document 10, compound number 45).

[Chemical Formula 4]

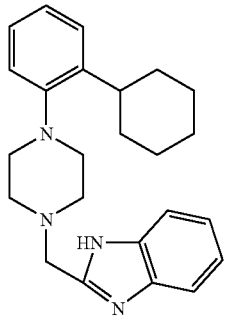

[Patent document 1] WO 2002/018320
[Patent document 2] WO 2002/059108
[Non-patent document 1] Inflammatory Bowel Disease (N. Engl. J. Med., 347:417-429(2002))
[Non-patent document 2] Natalizumab for active Crohn's disease (N. Engl. J. Med., 348:24-32(2003))
[Non-patent document 3] Granulocyte adsorption therapy in active period of ulcerative colitis (Japanese Journal of Apheresis 18:117-131(1999))
[Non-patent document 4] Rheumatoid arthritis (Int. J. Biochem. Cell Biol., 36:372-378(2004))
[Non-patent document 5] Psoriasis (Lancet, 361:1197-1204 (2003))
[Non-patent document 6] New and emerging treatment options for multiple sclerosis (Lancet Neurology, 2:563-566(2003))
[Non-patent document 7] The role of T lymphocytes in the pathogenesis of asthma (J. Allergy Clin. Immunol., 111: 450-463(2003))
[Non-patent document 8] The molecular basis of lymphocyte recruitment to the skin (J. Invest. Dermatol., 121:951-962 (2003))
[Non-patent document 9] A role for inflammation in irritable bowel syndrome (Gut., 51: i41-i44 (2002))
[Non-patent document 10] Discovery of 2-(4-pyridin-2-ylpiperazin-1-ylmethyl)-1H-benzimidazole (ABT-724), a dopaminergic agent with a novel mode of action for the potential treatment of erectile dysfunction (J. Med. Chem., 47: 3853-3864 (2004))

DISCLOSURE OF THE INVENTION

Problems to be Solved by the Invention

It is an object of the present invention to provide novel compounds having excellent cell adhesion inhibitory action and cell infiltration inhibitory action, which are useful as therapeutic or prophylactic agents for various inflammatory diseases and autoimmune diseases associated with adhesion and infiltration of leukocytes, such as inflammatory bowel disease (particularly ulcerative colitis or Crohn's disease), rheumatoid arthritis, irritable bowel syndrome, psoriasis, multiple sclerosis, asthma and atopic dermatitis.

Means for Solving the Problems

As a result of intensive research, the present inventors have discovered that salts and crystals of 1-cyclopropylmethyl-4-[2-(3,3,5,5-tetramethylcyclohexyl)phenyl]piperazine having novel chemical structure have excellent cell adhesion inhibitory action and cell infiltration inhibitory action, and are useful as therapeutic or prophylactic agents for various inflammatory diseases and autoimmune diseases associated with adhesion and infiltration of leukocytes, such as inflammatory bowel disease (particularly ulcerative colitis or Crohn's disease), irritable bowel syndrome, rheumatoid arthritis, psoriasis, multiple sclerosis, asthma and atopic dermatitis, and the present invention was completed on the basis of this discovery.

Specifically, the invention provides the [1] to [18] below.

[1] an acid salt of 1-cyclopropylmethyl-4-[2-(3,3,5,5-tetramethylcyclohexyl)phenyl]piperazine or hydrate thereof, wherein the acid is selected from the group consisting of methanesulfonic acid, hydrochloric acid, ethanesulfonic acid, benzenesulfonic acid, p-toluenesulfonic acid, hydrobromic acid and sulfuric acid.

[2] 1-cyclopropylmethyl-4-[2-(3,3,5,5-tetramethylcyclohexyl)phenyl]piperazine methanesulfonate or hydrate thereof.

[3] 1-cyclopropylmethyl-4-[2-(3,3,5,5-tetramethylcyclohexyl)phenyl]piperazine hydrochloride or hydrate thereof.

[4] 1-cyclopropylmethyl-4-[2-(3,3,5,5-tetramethylcyclohexyl)phenyl]piperazine ethanesulfonate or hydrate thereof.

[5] 1-cyclopropylmethyl-4-[2-(3,3,5,5-tetramethylcyclohexyl)phenyl]piperazine benzenesulfonate or hydrate thereof.

[6] 1-cyclopropylmethyl-4-[2-(3,3,5,5-tetramethylcyclohexyl)phenyl]piperazine p-toluenesulfonate or hydrate thereof.

[7] 1-cyclopropylmethyl-4-[2-(3,3,5,5-tetramethylcyclohexyl)phenyl]piperazine hydrobromide or hydrate thereof.

[8] 1-cyclopropylmethyl-4-[2-(3,3,5,5-tetramethylcyclohexyl)phenyl]piperazine sulfate or hydrate thereof.

[9] a crystal of 1-cyclopropylmethyl-4-[2-(3,3,5,5-tetramethylcyclohexyl)phenyl]piperazine methanesulfonate having a diffraction peak at a diffraction angle (2θ±0.2°) of 7.0° in a powder X-ray diffraction.

[10] the crystal according to [9] further having a diffraction peak at a diffraction angle (2θ±0.2°) of 18.3° in a powder X-ray diffraction.

[11] the crystal according to [10] further having diffraction peaks at diffraction angles (2θ±0.2°) of 13.1° and 15.4° in a powder X-ray diffraction.

[12] a crystal of 1-cyclopropylmethyl-4-[2-(3,3,5,5-tetramethylcyclohexyl)phenyl]piperazine methanesulfonate having peaks at chemical shifts of around 4.3 ppm and around 149.3 ppm in a $^{13}$C Solid State Nuclear Magnetic Resonance spectrum.

[13] the crystal according to [12] further having peaks at chemical shifts of around 121.5 ppm and around 143.8 ppm in a $^{13}$C Solid State Nuclear Magnetic Resonance spectrum.

[13-1] the crystal according to any one of [9] to [13], wherein the rate of 1-cyclopropylmethyl-4-[2-(3,3,5,5-tetramethylcyclohexyl)phenyl]piperazine to methanesulfonic acid is about 1:1.

[13-2] the crystal according to any one of [9] to [13] and [13-1], which is anhydrous crystal.

[14] a medicament comprising the salt of the compound or hydrate thereof according to any one of [1] to [13], [13-1] and [13-2].

[15] a cell adhesion inhibitor or cell infiltration inhibitor, comprising the salt of the compound or hydrate thereof according to any one of [1] to [13], [13-1] and [13-2].

[15-1] a therapeutic or prophylactic agent for inflammatory diseases and autoimmune diseases, comprising the salt of the compound or hydrate thereof according to any one of [1] to [13], [13-1] and [13-2].

[16] a therapeutic or prophylactic agent for inflammatory bowel disease, rheumatoid arthritis, psoriasis, multiple sclerosis, irritable bowel syndrome, asthma or atopic dermatitis, comprising the salt of the compound or hydrate thereof according to any one of [1] to [13], [13-1] and [13-2].

[17] a therapeutic or prophylactic agent for inflammatory bowel disease, comprising the salt of the compound or hydrate thereof according to any one of [1] to [13], [13-1] and [13-2].

[18] a therapeutic or prophylactic agent for ulcerative colitis or Crohn's disease, comprising the salt of the compound or hydrate thereof according to any one of [1] to [13], [13-1] and [13-2].

Effect of the Invention

Salts and crystals of the invention have excellent cell adhesion inhibitory action and cell infiltration inhibitory action, and therefore are useful as therapeutic or prophylactic agents for inflammatory diseases and autoimmune diseases, inter alia various diseases associated with adhesion and infiltration of leukocytes, such as inflammatory bowel disease (particularly ulcerative colitis or Crohn's disease), irritable bowel syndrome, rheumatoid arthritis, psoriasis, multiple sclerosis, asthma or atopic dermatitis.

Figure 1:
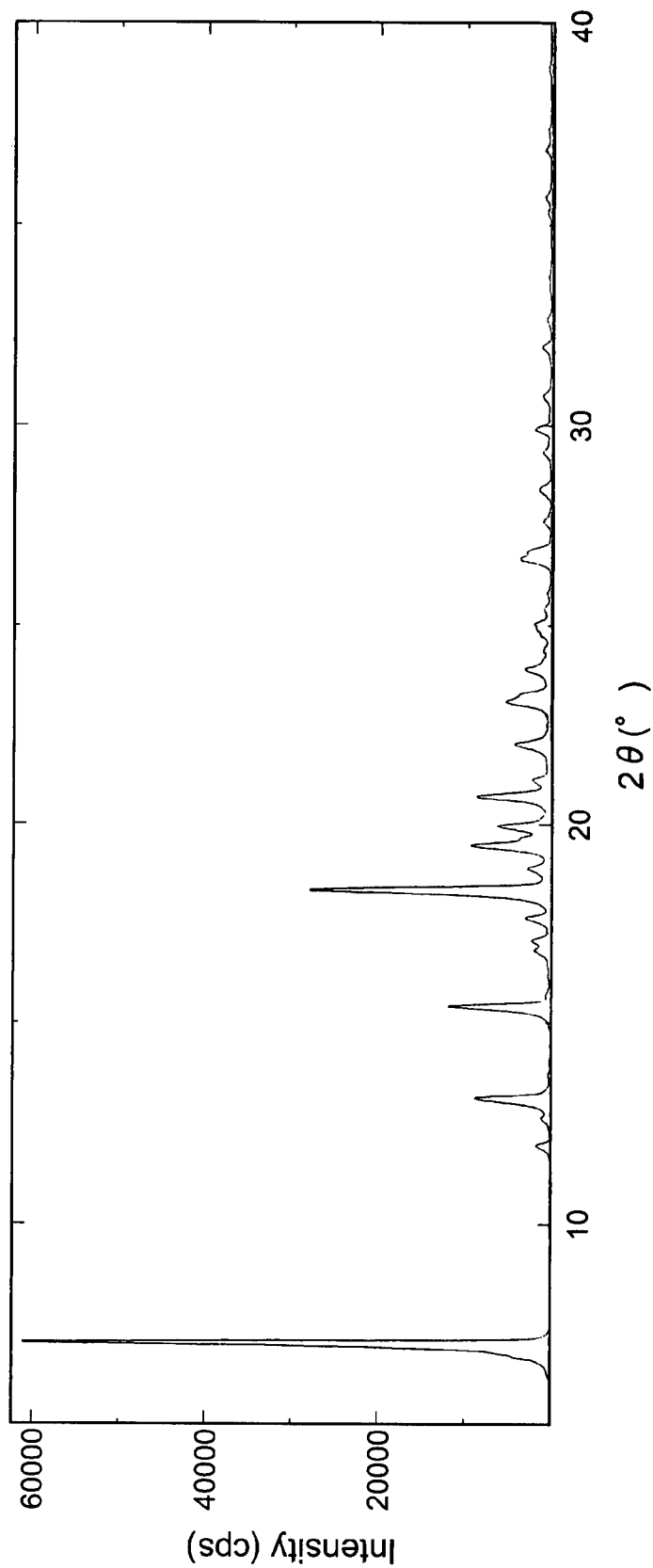
FIG. 1 shows a powder X-ray diffraction pattern of the crystal of 1-cyclopropylmethyl-4-[2-(3,3,5,5-tetramethylcyclohexyl)phenyl]piperazine methanesulfonate (crystal α) obtained in Example 1-G.
Figure 2:
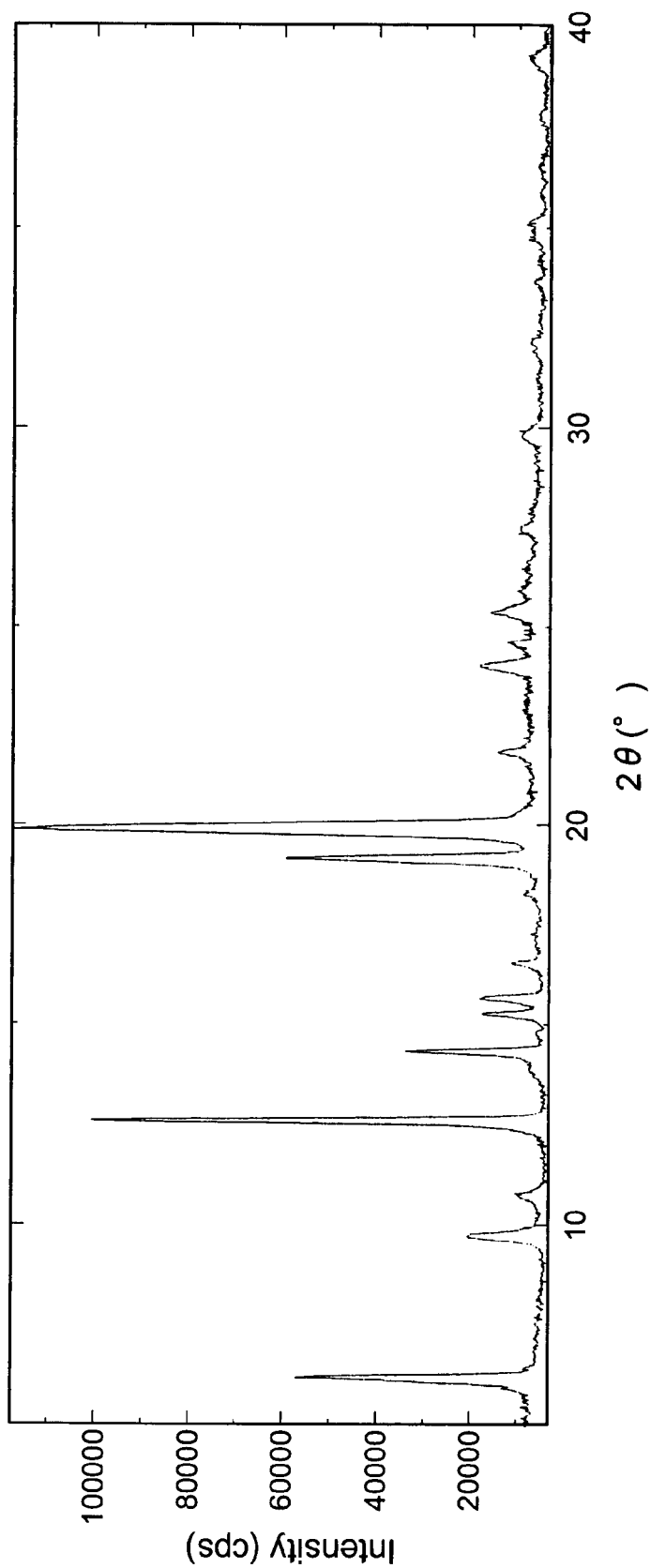
FIG. 2 shows a powder X-ray diffraction pattern of the crystal of 1-cyclopropylmethyl-4-[2-(3,3,5,5-tetramethylcyclohexyl)phenyl]piperazine (crystal A) obtained in Example 2.
Figure 3:
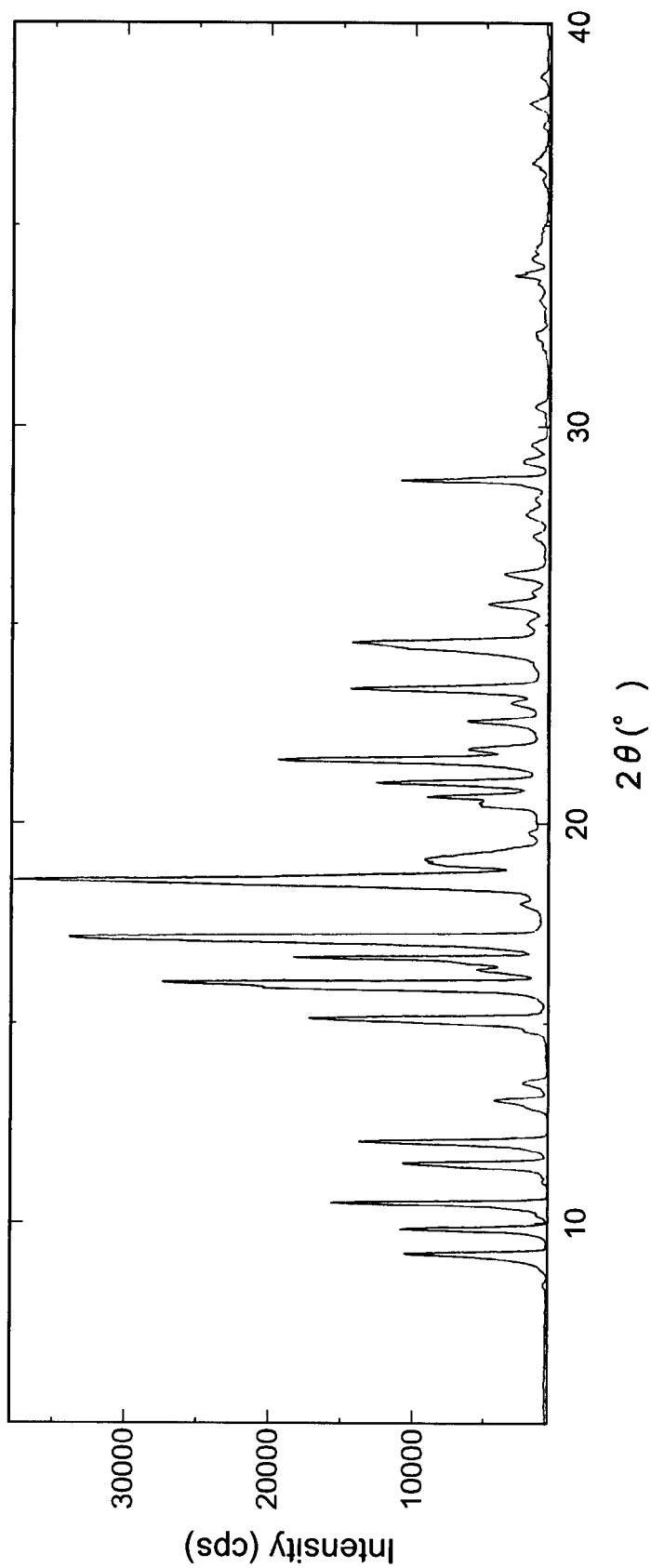
FIG. 3 shows a powder X-ray diffraction pattern of the crystal of 1-cyclopropylmethyl-4-[2-(3,3,5,5-tetramethylcyclohexyl)phenyl]piperazine (crystal B) obtained in Example 3.
Figure 4:
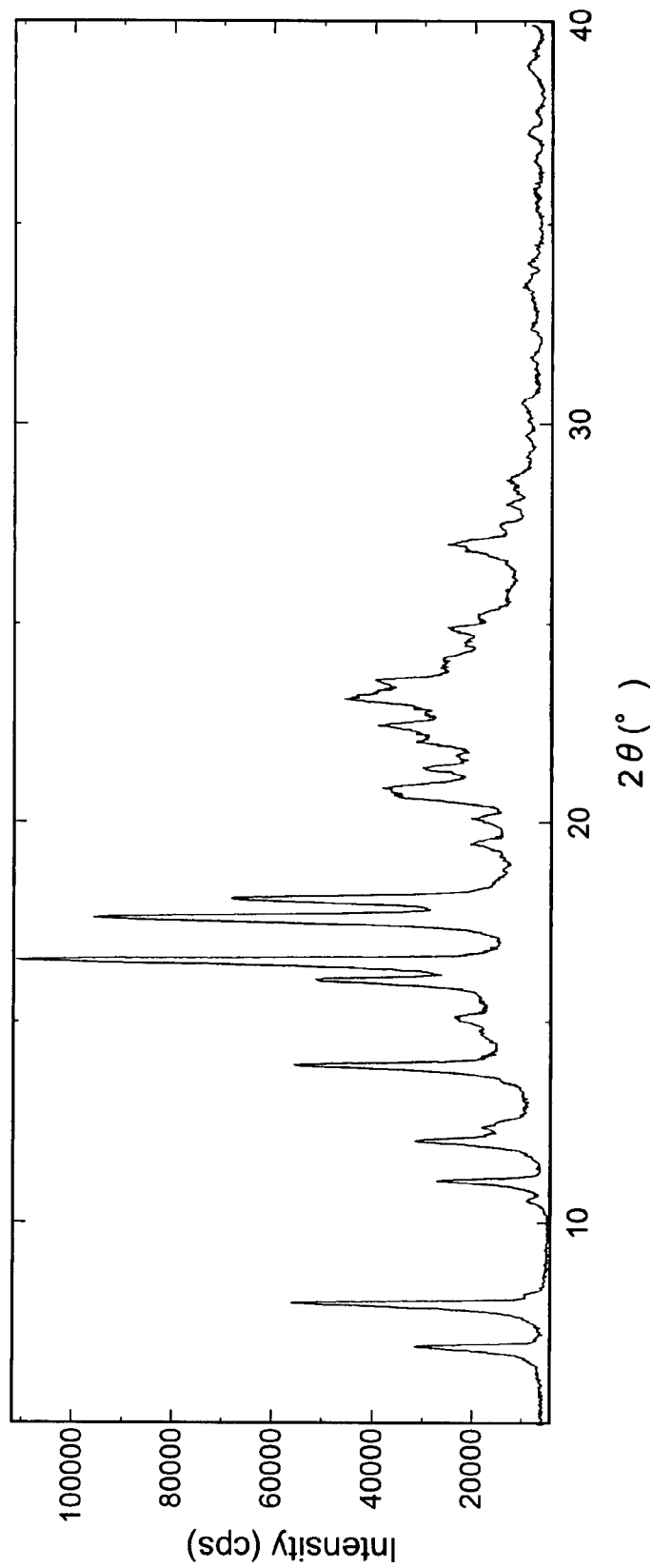
FIG. 4 shows a powder X-ray diffraction pattern of the crystal of 1-cyclopropylmethyl-4-[2-(3,3,5,5-tetramethylcyclohexyl)phenyl]piperazine benzenesulfonate obtained in Example 4.
Figure 5:
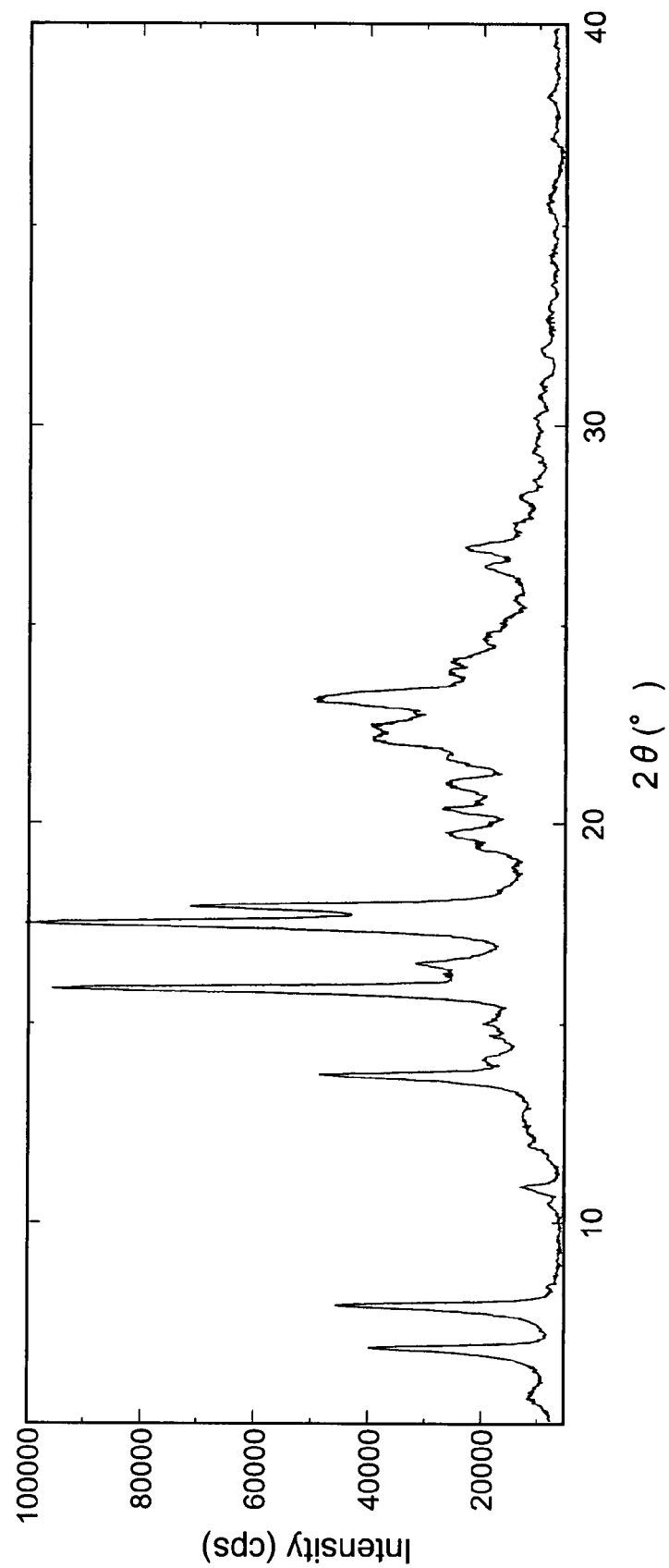
FIG. 5 shows a powder X-ray diffraction pattern of the crystal of 1-cyclopropylmethyl-4-[2-(3,3,5,5-tetramethylcyclohexyl)phenyl]piperazine p-toluenesulfonate obtained in Example 5.
Figure 6:
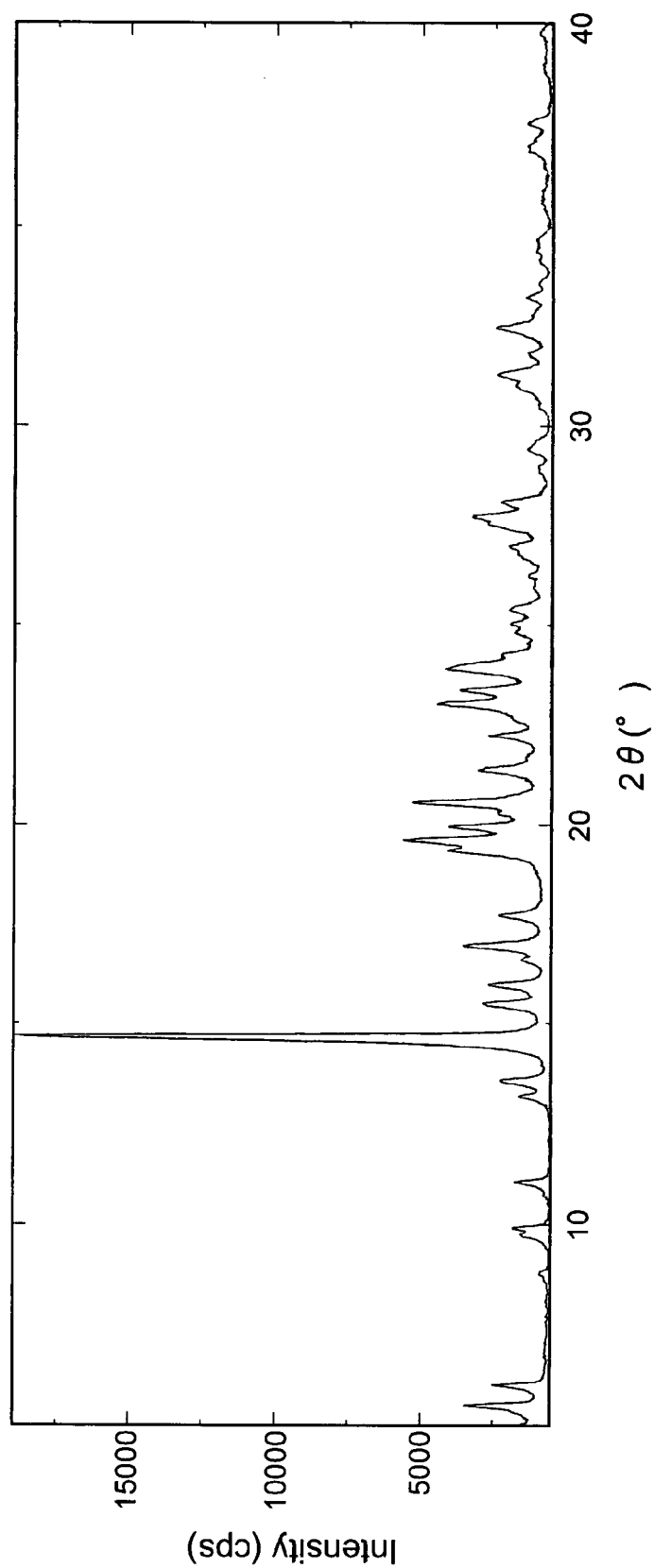
FIG. 6 shows a powder X-ray diffraction pattern of the crystal of 1-cyclopropylmethyl-4-[2-(3,3,5,5-tetramethylcyclohexyl)phenyl]piperazine hydrobromide obtained in Example 6.
Figure 7:
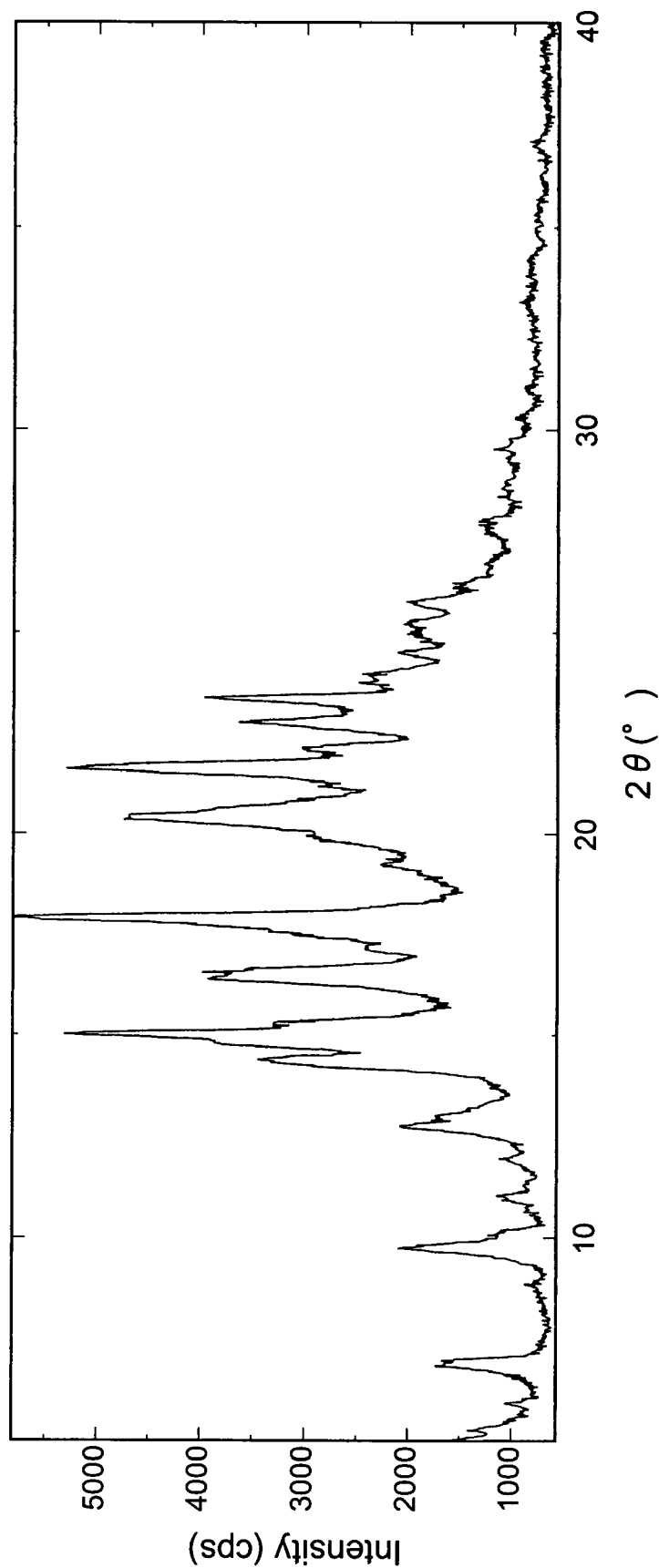
FIG. 7 shows a powder X-ray diffraction pattern of the crystal of 1-cyclopropylmethyl-4-[2-(3,3,5,5-tetramethylcyclohexyl)phenyl]piperazine sulfate (crystal a) obtained in Example 7.
Figure 8:
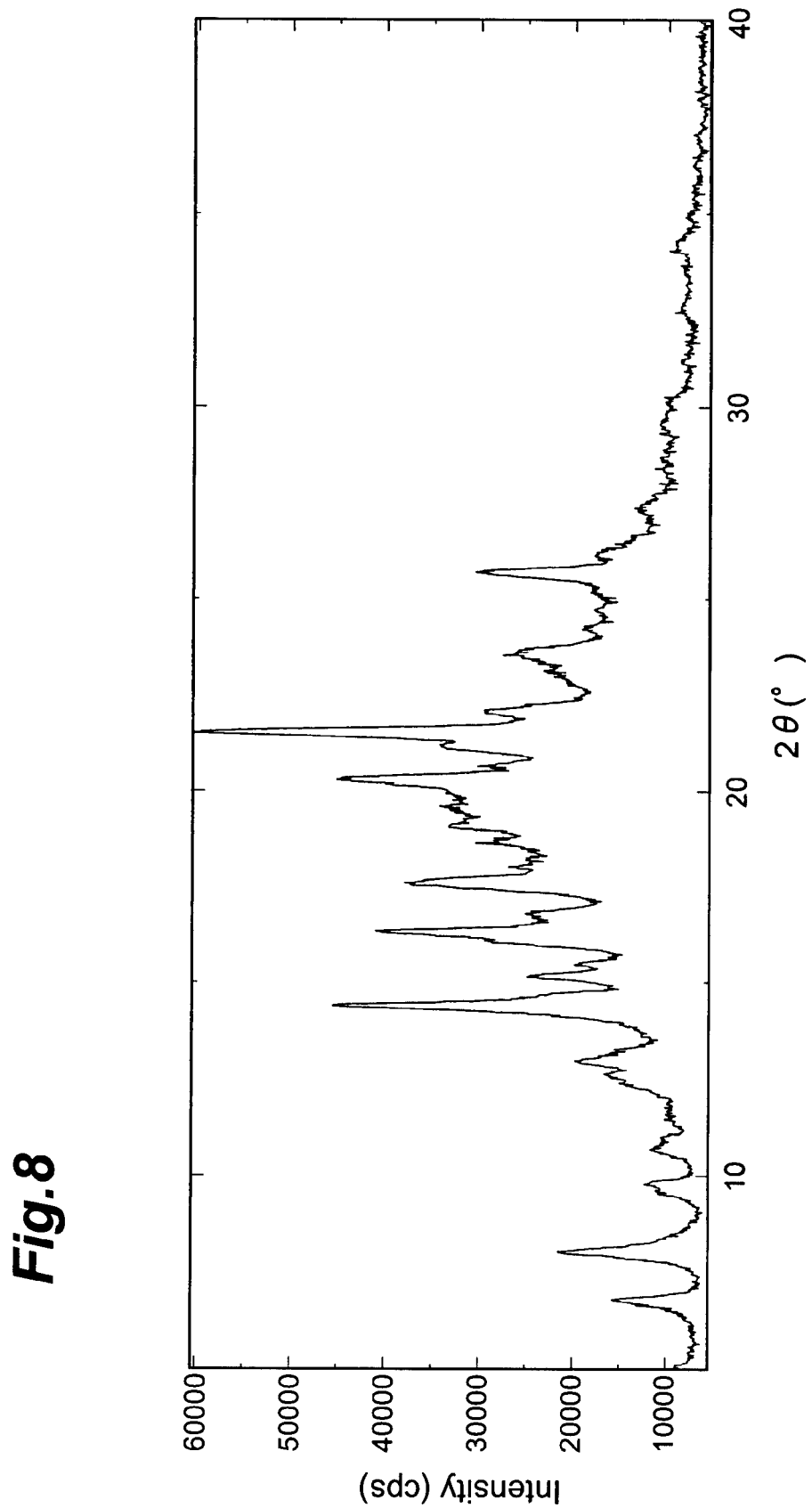
FIG. 8 shows a powder X-ray diffraction pattern of the crystal of 1-cyclopropylmethyl-4-[2-(3,3,5,5-tetramethylcyclohexyl)phenyl]piperazine sulfate (crystal b) obtained in Example 8.
Figure 9:
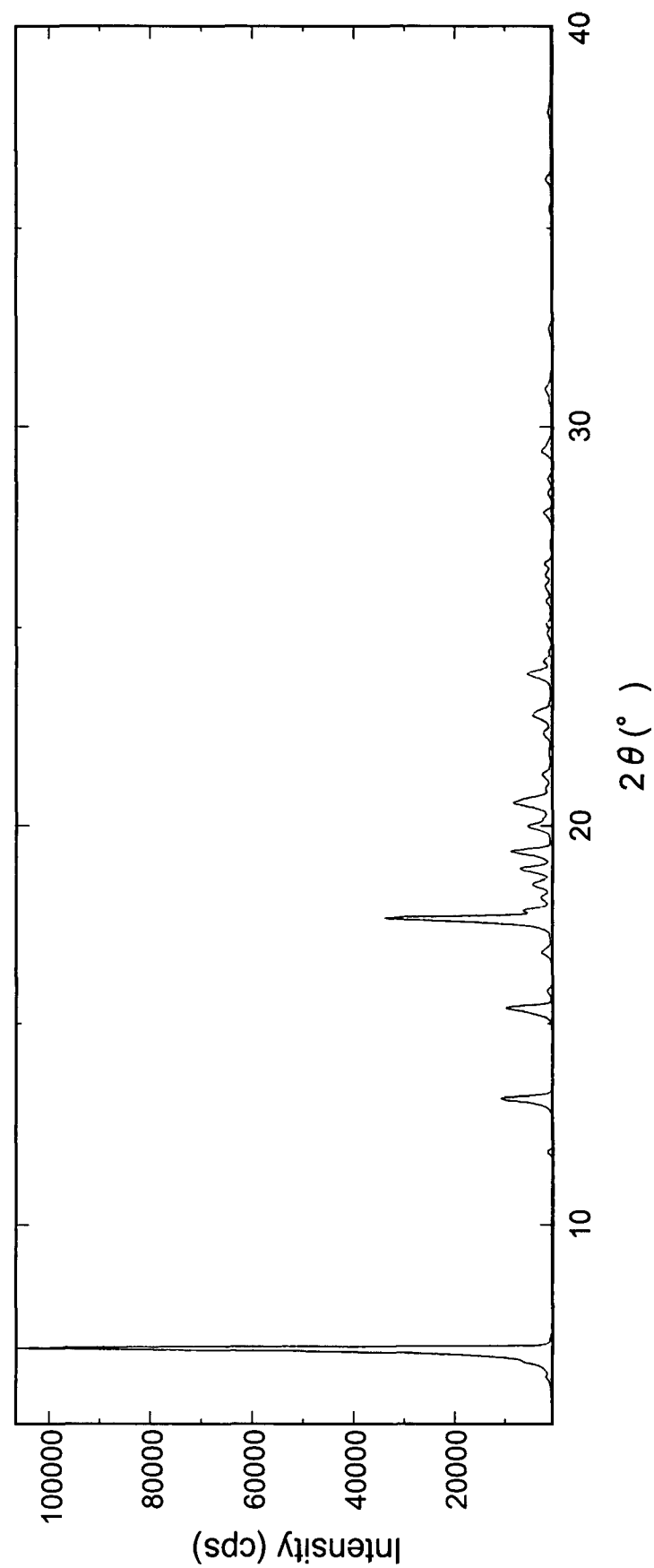
FIG. 9 shows a powder X-ray diffraction pattern of the crystal of 1-cyclopropylmethyl-4-[2-(3,3,5,5-tetramethylcyclohexyl)phenyl]piperazine ethanesulfonate obtained in Example 9.
Figure 10:
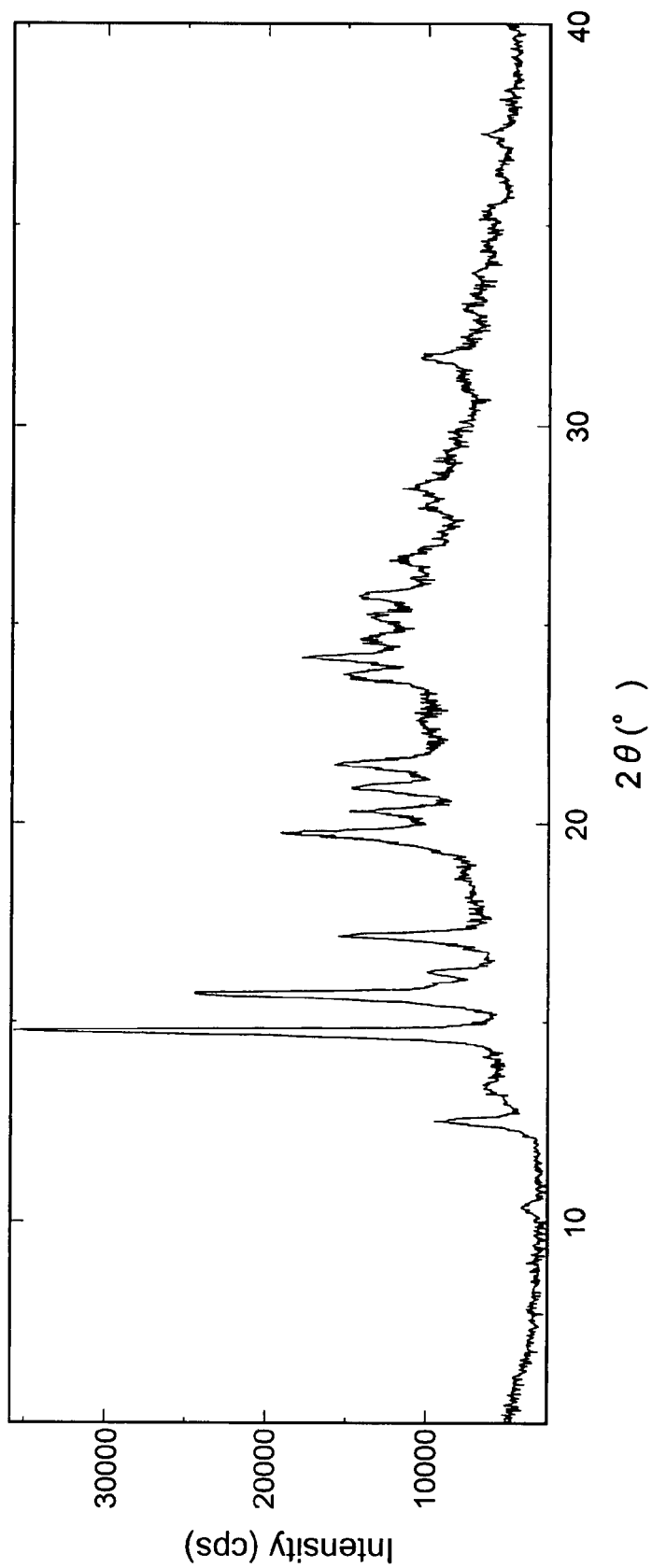
FIG. 10 shows a powder X-ray diffraction pattern of the crystal of 1-cyclopropylmethyl-4-[2-(3,3,5,5-tetramethylcyclohexyl)phenyl]piperazine hydrochloride (crystal II) obtained in Example 11.
Figure 11:
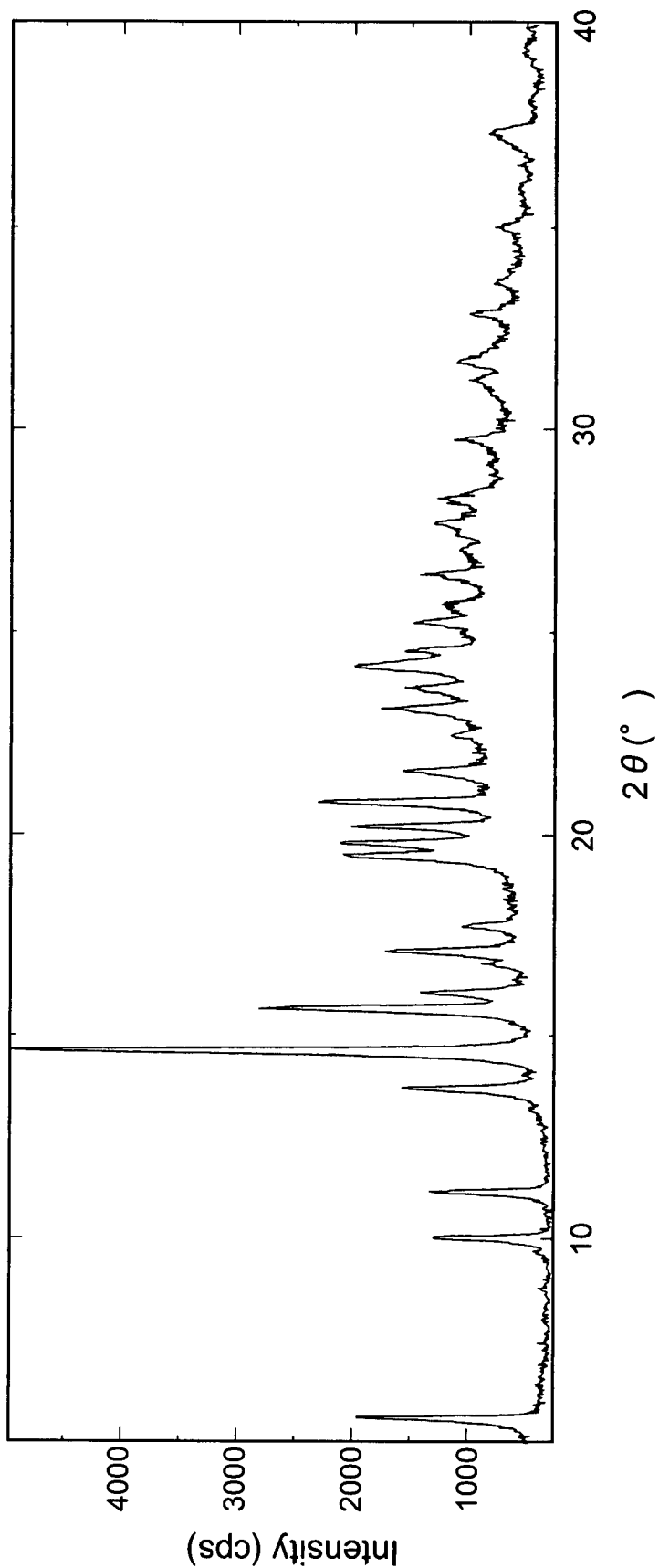
FIG. 11 shows a powder X-ray diffraction pattern of the crystal of 1-cyclopropylmethyl-4-[2-(3,3,5,5-tetramethylcyclohexyl)phenyl]piperazine hydrochloride (crystal I) obtained in Example 12.
Figure 12:
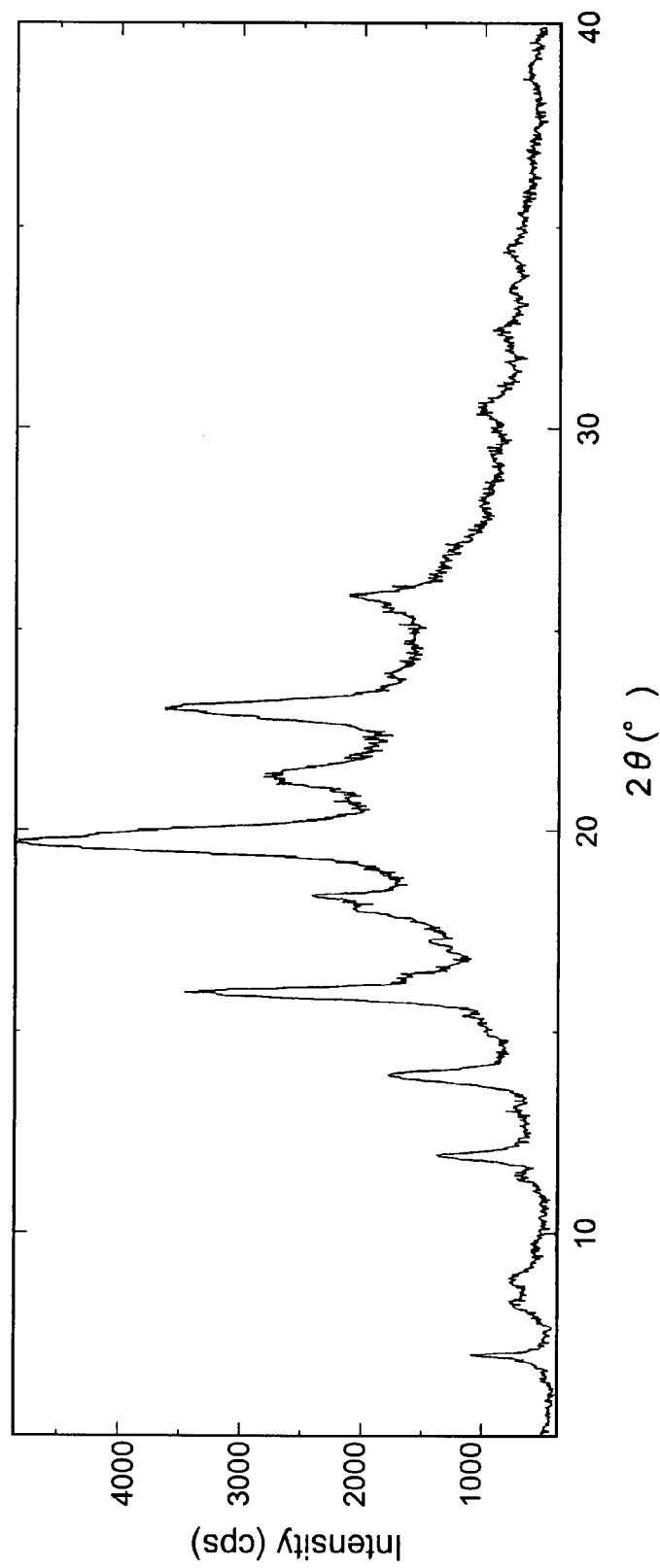
FIG. 12 shows a powder X-ray diffraction pattern of the crystal of 1-cyclopropylmethyl-4-[2-(3,3,5,5-tetramethylcyclohexyl)phenyl]piperazine methanesulfonate (crystal β) obtained in Example 13.
Figure 13:
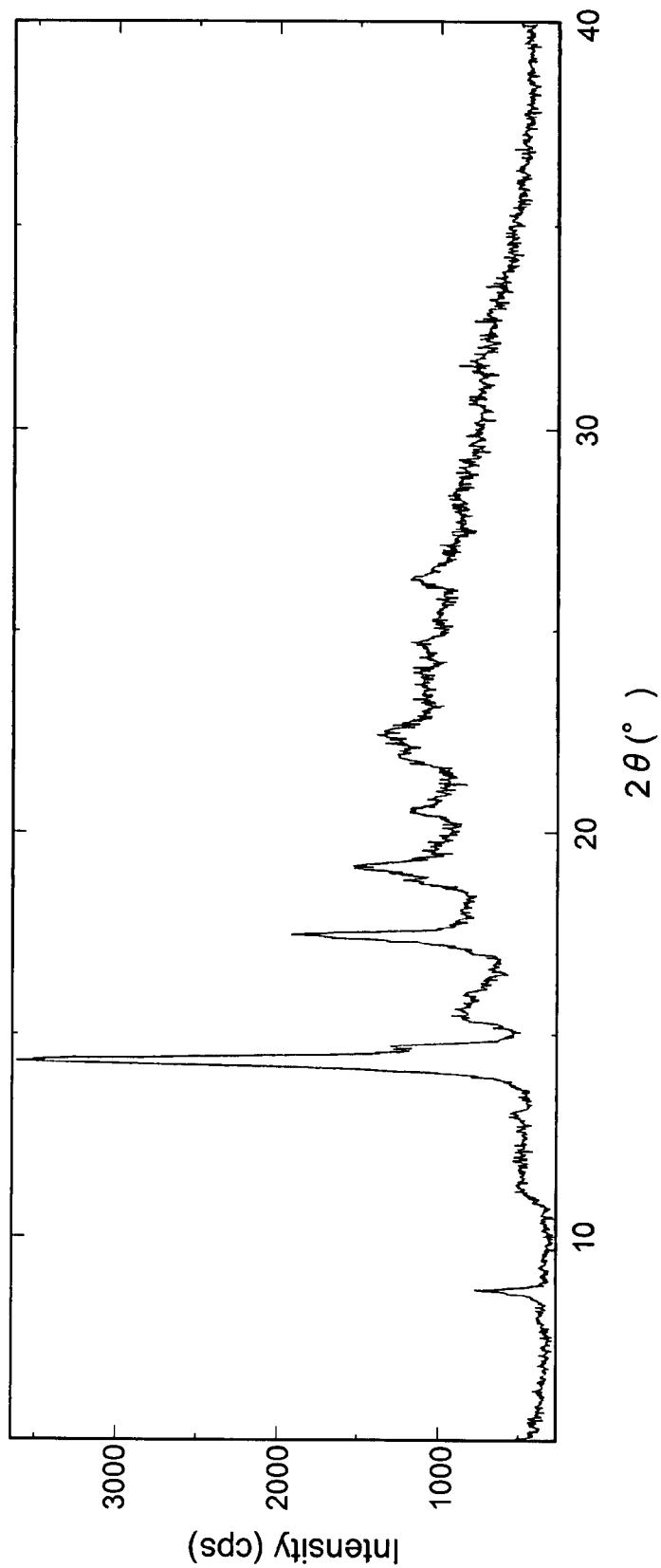
FIG. 13 shows a powder X-ray diffraction pattern of the crystal of 1-cyclopropylmethyl-4-[2-(3,3,5,5-tetramethylcyclohexyl)phenyl]piperazine hydrochloride (crystal III) obtained in Example 14.

BEST MODE FOR CARRYING OUT THE INVENTION (Salt of the Invention) The salt of the invention is an acid salt of 1-cyclopropylmethyl-4-[2-(3,3,5,5-tetramethylcyclohexyl)phenyl]piperazine, wherein the acid is selected from the group consisting of methanesulfonic acid, hydrochloric acid, ethanesulfonic acid, benzenesulfonic acid, p-toluenesulfonic acid, hydrobromic acid and sulfuric acid. The hydrate thereof is within the scope of the invention. These salt have cell adhesion inhibitory action and cell infiltration inhibitory action, and are useful as therapeutic or prophylactic agents for diseases such as inflammatory bowel disease.

The salt of the invention can be prepared by the following method. 1-Cyclopropylmethyl-4-[2-(3,3,5,5-tetramethylcyclohexyl)phenyl]piperazine and each acids are dissolve in an appropriate solvent, and the salt is precipitated. The precipitated salt is separated by usual filtration procedure, washed with an appropriate solvent (usually the same solvent as that used for precipitation) if necessary, and dried. To precipitate the salt, preferably an solvent is added to 1-cyclopropylmethyl-4-[2-(3,3,5,5-tetramethylcyclohexyl)phenyl]piperazine and each acid, the mixture is heated to form an dissolved state, then cooled.

1-Cyclopropylmethyl-4-[2-(3,3,5,5-tetramethylcyclohexyl)phenyl]piperazine used for preparation of salt can be any form, i.e. can be hydrate, anhydrous, amorphous and crystalline forms (including plural crystal polymorphs) and may even be a mixture thereof.

The solvent to be used typically includes, but not limited to, ketones such as methyl ethyl ketone and acetone, alcohols such as methanol and ethanol, esters such as ethyl acetate and methyl acetate, hydrocarbons such as hexane and heptane, ethers such as tetrahydrofuran, diethyl ether and dioxane, dimethylsulfoxide, dimethylformamide or water, or mixed solvent thereof. The amount of the solvent used may appropriately be selected between the lower limit and the upper limit, the lower limit being an amount to dissolve 1-cyclopropylmethyl-4-[2-(3,3,5,5-tetramethylcyclohexyl)phenyl]piperazine and each acid by heating and the upper limit being an amount so as not to significantly reduce the yield of the salt. The temperature at which 1-cyclopropylmethyl-4-[2-(3,3,5, 5-tetramethylcyclohexyl)phenyl]piperazine and each acid are dissolved by heating may appropriately be selected depending on the solvent. The final cooled temperature may also appropriately be selected in consideration of the yield and the quality of the salt, or the like; and it is preferably from room temperature to 0° C.

The salt of the invention may be precipitated by adding a poor solvent, i.e. a solvent having lower solubility of 1-cyclopropylmethyl-4-[2-(3,3,5,5-tetramethylcyclohexyl)phenyl]piperazine and each acid, to a solution of 1-cyclopropylmethyl-4-[2-(3,3,5,5-tetramethylcyclohexyl)phenyl]piperazine and each acid.

The salt separated by the filtration can be dried by allowing it to stand in the atmosphere, but it is not effective for large scale production, therefore drying by heating is preferable. Drying temperature may appropriately be selected depending on the production quantity. Drying time may appropriately be selected as the time during which the residual solvent is removed below the prescribed amount depending on the production quantity, drying apparatus, drying temperature or the like. Drying can be performed either under aeration or under reduced pressure, and drying under reduced pressure is preferable. The level of pressure reduction may appropriately be selected, depending on the production quantity, drying apparatus, drying temperature or the like.

(Crystal of the Invention)

The crystal of the invention is a uniform crystal of 1-cyclopropylmethyl-4-[2-(3,3,5,5-tetramethylcyclohexyl)phenyl]piperazine methanesulfonate, and characterized in having a diffraction peak at a diffraction angle (2θ±0.2°) of 7.0° in a powder X-ray diffraction, further characterized in having a diffraction peak at 18.3°, and further characterized in having diffraction peaks at 13.1° and 15.4°.

As for a diffraction angle (2θ) in the powder X-ray diffraction analysis, errors in the diffraction angle, generally, may occur within the range of ±0.2°. It is, therefore, to be understood that the values of the diffraction angles may include numerals on the order of ±0.2°. Accordingly, the invention encompasses not only crystal having completely matching diffraction angles of the peaks in powder X-ray diffraction, but also crystal having matching diffraction angles of the peaks within the errors of about ±0.2°.

The crystal of the invention is characterized in having peaks at chemical shifts of around 4.3 ppm and around 149.3 ppm in a $^{13}C$ Solid State NMR spectrum, and further characterized in having peaks at chemical shifts of around 121.5 ppm and around 143.8 ppm.

In this Specification, "having peaks at chemical shifts of around 4.3 ppm and around 149.3 ppm" means "having peaks substantially equivalent to 4.3 ppm and 149.3 ppm when a $^{13}C$ Solid State NMR spectrum is measured under normal conditions or under the conditions substantially the same as those described in this Specification".

In this Specification, "having peaks at chemical shifts of around 121.5 ppm and around 143.8 ppm" means "having peaks substantially equivalent to 121.5 ppm and 143.8 ppm when a $^{13}C$ Solid State NMR spectrum is measured under normal conditions or under the conditions substantially the same as those described in this Specification".

The crystal of the invention can be prepared by the following method. 1-Cyclopropylmethyl-4-[2-(3,3,5,5-tetramethylcyclohexyl)phenyl]piperazine and methanesulfonic acid are added in an appropriate solvent such as methyl ethyl ketone, and the mixture is heated to form a thoroughly dissolves state, and the mixture is slowly cooled to precipitate the methanesulfonate. At this point, the precipitated crystals of the salt can be collected by filtration and dried to give the compound of interest, but the following procedure may be continued. The obtained suspension is concentrated under reduced pressure and dried under reduced pressure to give the methanesulfonate as a solid. To the solid is added an appropriate solvent such as a mixed solvent of ethyl acetate and heptane, and the mixture is heated, the suspension containing the solid is slowly cooled to precipitate crystals. The precipitated crystals is separated by usual filtration procedure, washed with an appropriate solvent such as a mixed solvent of ethyl acetate and heptane if necessary, and dried.

The crystals separated by the filtration can be dried by allowing them to stand in the atmosphere, but it is not effective for large scale production, therefore drying by heating is preferable. Drying temperature may appropriately be selected depending on the production quantity. Drying time may appropriately be selected as the time during which the residual solvent is removed below the prescribed amount depending on the production quantity, drying apparatus, drying temperature or the like. Drying can be performed either under aeration or under reduced pressure, and drying under reduced pressure is preferable. The level of pressure reduction may appropriately be selected, depending on the production quantity, drying apparatus, drying temperature or the like.

1-Cyclopropylmethyl-4-[2-(3,3,5,5-tetramethylcyclohexyl)phenyl]piperazine used for preparation of the salt or crystal of the invention may be synthesized according to the following reaction scheme. For detailed reaction conditions, see Example 1-A to Example 1-F.

[Chemical Formula 5]

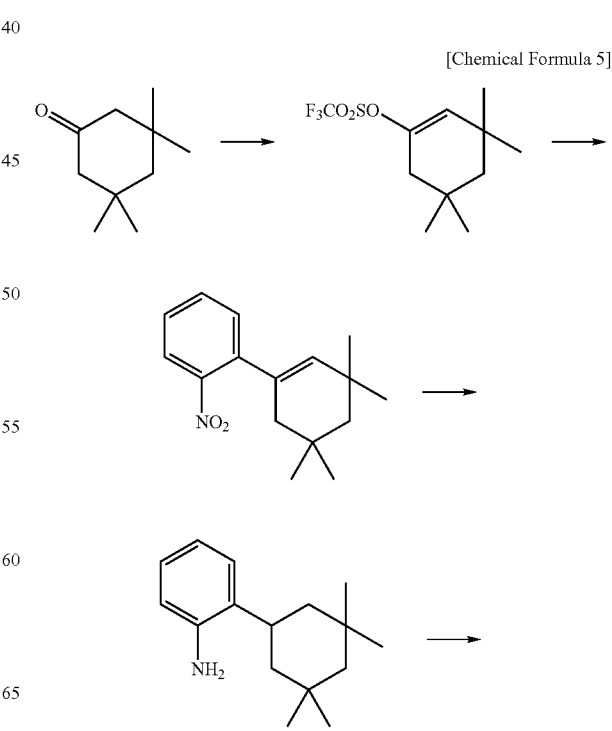

-continued

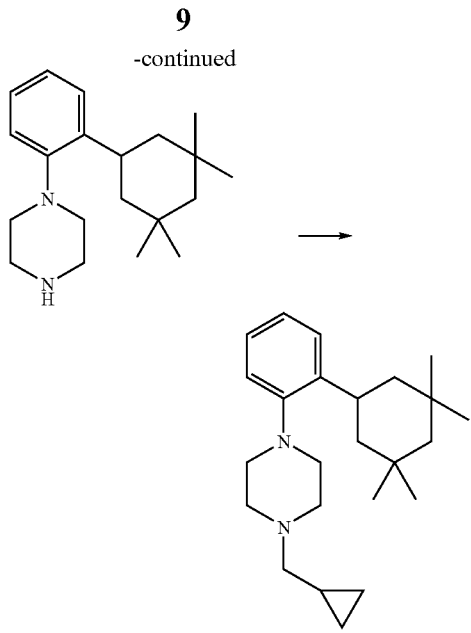

When the salt or crystal of the invention is to be used as a medicament, it is normally compounded with suitable pharmaceutical ingredients to prepare pharmaceutical products for use. Notwithstanding, the use of a drug substance form of the salt or crystal of the invention as a medicament should not be negated.

The pharmaceutical ingredients may include excipients, binders, lubricants, disintegrating agents, coloring agents, taste correctives, emulsifiers, surfactants, dissolving aids, suspending agents, isotonizing agents, buffering agents, preservatives, antioxidants, stabilizers, absorption enhancers, and the like, all of which are generally used in medicaments. If desired, these agents may be combined for use.

The excipients may include, for example, lactose, white soft sugar, glucose, corn starch, mannitol, sorbitol, starch, alpha starch, dextrin, crystalline cellulose, light silicic anhydride, aluminum silicate, calcium silicate, magnesium aluminometasilicate, calcium hydrogenphosphate, and the like.

The binders may include, for example, polyvinyl alcohol, methylcellulose, ethylcellulose, gum Arabic, tragacanth, gelatin, shellac, hydroxypropylmethylcellulose, hydroxypropylcellulose, carboxymethylcellulose sodium, polyvinylpyrrolidone, macrogol, and the like.

The lubricants may include, for example, magnesium stearate, calcium stearate, sodium stearyl fumarate, talc, polyethylene glycol, colloidal silica, and the like.

The disintegrating agents may include, for example, crystalline cellulose, agar, gelatin, calcium carbonate, sodium hydrogencarbonate, calcium citrate, dextrin, pectin, low-substituted hydroxypropylcellulose, carboxymethylcellulose, carboxymethylcellulose calcium, croscarmellose sodium, carboxymethyl starch, carboxymethyl starch sodium, and the like.

The coloring agents may include iron sesquioxide, yellow iron sesquioxide, carmine, caramel, beta-carotene, titanium oxide, talc, riboflavin sodium phosphate, yellow aluminum lake, and the like, which have been approved as additives for medicaments.

The taste correctives agents may include cocoa powder, menthol, aromatic powder, mentha oil, borneol, powdered cinnamon bark, and the like The emulsifiers or the surfactants may include stearyl triethanolamine, sodium lauryl sulfate, lauryl aminopropionic acid, lecithin, glycerin monostearate, sucrose fatty acid ester, glycerin fatty acid ester, and the like.

The dissolving aids may include polyethylene glycol, propylene glycol, benzyl benzoate, ethanol, cholesterol, triethanolamine, sodium carbonate, sodium citrate, Polysorbate 80, nicotinamide, and the like.

The suspending agents may include, in addition to the surfactants, hydrophilic polymers such as polyvinyl alcohol, polyvinylpyrrolidone, methylcellulose, hydroxymethylcellulose, hydroxyethylcellulose, and hydroxypropylcellulose.

The isotonizing agents may include glucose, sodium chloride, mannitol, sorbitol and the like.

The buffering agents may include the buffers of phosphate, acetate, carbonate, citrate and the like.

The preservatives may include methylparaben, propylparaben, chlorobutanol, benzyl alcohol, phenethyl alcohol, dehydroacetic acid, sorbic acid and the like.

The antioxidants may include sulfite, ascorbic acid, alpha-tocopherol and the like.

The stabilizers may include those generally used in medicaments.

The absorption enhancers may include those generally used in medicaments.

The pharmaceutical products may include: oral agents such as tablets, powders, granules, capsules, syrups, troches, and inhalations; external preparations such as suppositories, ointments, ophthalmic ointments, tapes, ophthalmic solutions, nasal drops, ear drops, poultices, and lotions; and injections.

The oral agents may appropriately be combined with the auxiliaries described above to form preparations. In addition, the surfaces of the agents may be coated if necessary.

The external preparations may appropriately be combined with the auxiliaries described above, in particular, excipients, binders, taste correctives, emulsifiers, surfactants, dissolving aids, suspending agents, isotonizing agents, preservatives, antioxidants, stabilizers or absorption enhancers to form the preparations.

The injections may appropriately be combined with the auxiliaries described above, in particular, emulsifiers, surfactants, dissolving aids, suspending agents, isotonizing agents, preservatives, antioxidants, stabilizers, or absorption enhancers to form the preparations.

When the salt and the crystal of the invention is to be used as a medicament, its dosage level may differ depending on the symptoms, ages or others, but it is normally given in a single administration or in divided administrations 2 to 6 times daily at the following doses: from 0.15 to 5000 mg (preferably from 0.5 to 1500 mg) in the case of an oral agent; from 0.5 to 1500 mg (preferably from 1.5 to 500 mg) in the case of an external preparation; and 0.3 to 5000 mg (preferably from 1 to 500 mg) in the case of an injection. Here, the actual amounts to be administered are indicated with respect to the oral agent and the injection, while the amount to be absorbed by the body is indicated with respect to the external preparation.

EXAMPLES

Silica gel used in the following Examples are silica gel 60 (Merck & Co., Inc) or BW300 (Fuji Silysia Chemical Ltd.) unless otherwise mentioned, and NH silica gel used are Chromatorex-NH silica gel (Fuji Silysia Chemical Ltd.), propylamine-coated one.

(Synthesis of Compounds)

Example 1

1-Cyclopropylmethyl-4-[2-(3,3,5,5-tetramethylcyclohexyl)phenyl]piperazine methanesulfonate

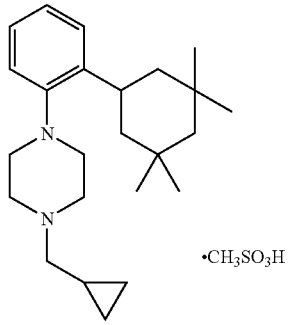

[Chemical Formula 6]

·CH₃SO₃H

Example 1-A

Trifluoromethanesulfonic acid 3,3,5,5-tetramethylcyclohex-1-enyl ester

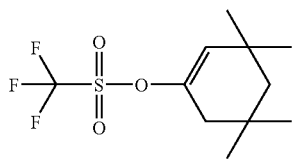

[Chemical Formula 7]

3,3,5,5-Tetramethylcyclohexanone (100.0 g, 648.3 mmol) was dissolved in anhydrous tetrahydrofuran (750 mL) under a nitrogen atmosphere, and the mixture was cooled and stirred at an external temperature of below −70° C. To the mixture was added dropwise bis(trimethylsilyl)amide lithium (1 M solution in tetrahydrofuran, 778 mL, 778 mmol) over a period of 30 minutes under the same conditions, followed by stirring for 70 minutes under the same conditions. Then, a solution of N-phenylbis(trifluoromethanesulfonimide) (254.8 g, 713 mmol) in anhydrous tetrahydrofuran (1 L) was added dropwise to the reaction mixture over a period of 35 minutes. After stirring the mixture for 20 minutes under the same conditions, the mixture was stirred for 15 hours while gradually warmed to an external temperature of room temperature. Reaction was repeated twice more on the same scale as above, by the same procedure under the same reaction conditions. The three reaction mixtures were combined and subjected to the following treatment.

Ethyl acetate (1.5 L) was added to the combined reaction mixture, and then a solution of concentrated hydrochloric acid (450 mL) in ice water (5 L) was added while stirring. After stirring for a while, the separated organic layer was washed with brine (1.5 L), a saturated aqueous solution of sodium hydrogencarbonate (1.5 L) and brine (1.5 L). The obtained organic layer was dried over anhydrous magnesium sulfate (1 kg) for 30 minutes while stirring. The desiccant was removed by filtration and the filtrate was concentrated under reduced pressure. The resultant residue was purified by silica gel column chromatography (hexane) and then dried under reduced pressure to give 520.94 g of the title compound as a light yellow oil.

$^1$H-NMR (400 MHz, CDCl₃) δ: 1.05 (s, 6H), 1.10 (s, 6H), 1.35 (s, 2H), 2.09 (d, J=1.2 Hz, 2H), 5.51 (t, J=1.2 Hz, 1H).

Example 1-B

1-Nitro-2-(3,3,5,5-tetramethylcyclohex-1-enyl)benzene

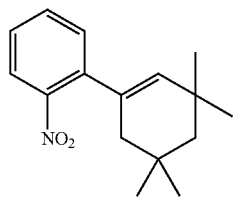

[Chemical Formula 8]

To a mixture of trifluoromethanesulfonic acid 3,3,5,5-tetramethylcyclohex-1-enyl ester (160.0 g, 558.8 mmol), 2-nitrophenylboronic acid (97.9 g, 586.8 mmol) and 1,2-dimethoxyethane (920 mL) were added sodium carbonate (118.5 g, 1.12 mol) and purified water (230 mL) while stirring at room temperature. Then, tetrakis(triphenylphosphine)palladium(0) (29.1 g, 25.1 mmol) was added to the mixture at room temperature (in an oil bath at room temperature), and the inside of the flask was replaced with nitrogen gas. The mixture was then stirred for 4 hours and 30 minutes at an external temperature of room temperature (in an oil bath at room temperature).

The same reaction was then repeated twice more by the same procedure under the same reaction conditions as above, but with an amount of 170.0 g (593.7 mmol) of trifluoromethanesulfonic acid 3,3,5,5-tetramethylcyclohex-1-enyl ester, a starting material, and the amounts of the other reagents changed to corresponding equivalents. The three reaction mixtures were combined and subjected to the following treatment.

Ethyl acetate (1.5 L) and water (4 L) were added to the combined reaction mixture, which was then stirred for 5 minutes. The mixture was filtered through Celite to remove insoluble materials. After stirring the obtained filtrate for a while, the organic layer was separated and the aqueous layer was extracted with ethyl acetate (1 L). The organic layers were combined and then dried over anhydrous magnesium sulfate (1 kg) for 20 minutes while stirring. The desiccant was removed by filtration and the filtrate was concentrated under reduced pressure. The resultant residue was purified by silica gel column chromatography (ethyl acetate/hexane) and then dried under reduced pressure to give 407.30 g of the title compound as a yellow solid.

$^1$H-NMR (400 MHz, CDCl₃) δ: 1.046 (s, 6H), 1.053 (s, 6H), 1.41 (s, 2H), 2.02 (d, J=1.6 Hz, 2H), 5.37 (t, J=1.6 Hz, 1H), 7.26 (dd, J=7.6, 1.6 Hz, 1H), 7.33 (ddd, J=8.0, 7.6, 1.6 Hz, 1H), 7.49 (ddd, J=7.6, 7.6, 1.2 Hz, 1H), 7.74 (dd, J=8.0, 1.2 Hz, 1H).

Example 1-C 2-(3,3,5,5-Tetramethylcyclohexyl)phenylamine

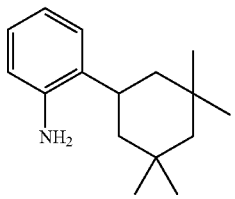

[Chemical Formula 9]

A mixture of 1-nitro-2-(3,3,5,5-tetramethylcyclohex-1-enyl)benzene (130.0 g, 501.3 mmol), 10% palladium on carbon (13.0 g, wet) and ethyl alcohol (1820 mL) was placed in a flask, then the inside of the flask was replaced with hydrogen, and the mixture was stirred for 78 hours at room temperature under a hydrogen atmosphere at atmospheric pressure. Reaction was repeated two more times on the same scale as above, by the same procedure under the same reaction conditions. The three reaction mixtures were combined and subjected to the following treatment.

The combined reaction mixture was filtered, and the filtrate was concentrated under reduced pressure. The obtained residue was diluted with ethyl acetate (700 mL) and hexane (200 mL), and then dried over anhydrous sodium sulfate (200 g) for 20 minutes while stirring. The desiccant was removed using a glass microfibre filter, and then the filtrate was concentrated and dried under reduced pressure to give 345.76 g of the title compound as a light brown oil.

$^1$H-NMR (400 MHz, CDCl$_3$) δ: 0.95 (s, 6H), 1.13 (s, 6H), 1.08-1.36 (m, 4H), 1.59-1.62 (m, 2H), 2.86 (tt, J=12.4, 2.8 Hz, 1H), 3.63 (brs, 2H), 6.70 (dd, J=7.6, 1.2 Hz, 1H), 6.78 (ddd, J=7.6, 7.6, 1.2 Hz, 1H), 7.02 (ddd, J=7.6, 7.6, 1.2 Hz, 1H), 7.12 (dd, J=7.6, 1.2 Hz, 1H).

Example 1-D

1-[2-(3,3,5,5-Tetramethylcyclohexyl)phenyl]piperazine

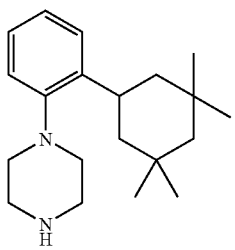

[Chemical Formula 10]

To a mixture of 2-(3,3,5,5-tetramethylcyclohexyl)phenylamine (168.0 g, 726.1 mmol) and 1,2-dichlorobenzene (1200 mL) was added bis(2-chloroethyl)amine hydrochloride (155.5 g, 871.3 mmol). The mixture was stirred for 7 hours at an external temperature of 190° C. under a nitrogen atmosphere. During the reaction, a nitrogen stream was passed through the reactor several times to remove the generated hydrogen chloride gas. Reaction was repeated once more on the same scale as above, by the same procedure under the same reaction conditions. The two reaction mixtures were combined and subjected to the following treatment.

After cooling to room temperature, the combined reaction mixture was diluted with ethyl acetate (6 L) and water (1 L). The mixture was then added to a mixture of potassium carbonate (1.3 kg) and water (5 L) while stirring. The mixture was stirred and allowed to stand, and the organic layer was separated. The aqueous layer was again extracted with ethyl acetate (2 L). The combined organic layers were washed with brine (3 L) and then dried over anhydrous sodium sulfate (3.5 kg). The desiccant was removed by filtration and the filtrate was concentrated under reduced pressure. The resultant residue was purified by NH silica gel column chromatography (ethyl acetate/hexane) and then dried under reduced pressure to give 241.67 g of the title compound as a light pink solid.

In addition to this, the above NH silica gel column chromatography purification also yielded 126.2 g of an oil as a mixture of the target compound and impurities. Hexane (150 mL) was added to the oil, and the mixture was stirred for 2 hours at 0° C. The produced precipitate was collected by suction filtration and then dried under reduced pressure to give 42.74 g of the title compound as a light pink solid. A total of 284.41 g of the title compound was obtained as a light pink solid.

$^1$H-NMR (400 MHz, CDCl$_3$) δ: 0.93 (s, 6H), 1.13 (s, 6H), 1.17-1.35 (m, 4H), 1.42-1.46 (m, 2H), 2.84-2.87 (m, 4H), 3.02-3.04 (m, 4H), 3.60 (tt, J=12.8, 2.8 Hz, 1H), 7.06-7.18 (m, 3H), 7.23 (dd, J=7.6, 1.6 Hz, 1H). The 1H of NH could not be identified.

Example 1-F

1-Cyclopropylmethyl-4-[2-(3,3,5,5-tetramethylcyclohexyl)phenyl]piperazine

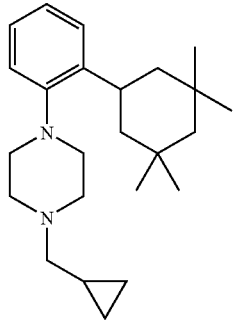

[Chemical Formula 11]

To a mixture of 1-[2-(3,3,5,5-tetramethylcyclohexyl)phenyl]piperazine (241.67 g, 804.3 mmol), acetic acid (46.0 mL, 804.3 mmol) and tetrahydrofuran (3300 mL) was added a mixed solution of cyclopropanecarbaldehyde (64.8 g, 924.9 mmol) and tetrahydrofuran (200 mL) while stirring at an external temperature of room temperature. After stirring for 10 minutes, sodium triacetoxyborohydride (238.6 g, 1126 mmol) was added portionwise to the reaction mixture over a period of 8 minutes. The mixture was then stirred for 3 hours at an external temperature of room temperature.

The reaction mixture was diluted with hexane (2 L) and water (1 L). This mixture was then added to a mixture of potassium carbonate (667 g) and water (3.5 L) while stirring. After stirring for a while and allowing the mixture to stand, the separated organic layer was washed sequentially with water (2 L) and brine (1.5 L). The organic layer was then dried over anhydrous sodium sulfate (1.5 kg), the desiccant was removed by filtration, and the obtained filtrate was concentrated under reduced pressure. The obtained residue was purified by NH silica gel column chromatography (ethyl acetate/hexane) and then concentrated under reduced pressure to give an oil. The oil was dissolved again in ethyl acetate (IL), and the mixture was filtered through a glass microfibre filter to remove insoluble materials. The obtained filtrate was concentrated under reduced pressure, and then a vacuum pump was used for drying under reduced pressure for 2 hours at an external temperature of 50° C., to give 280.7 g of the title compound as crystals.

$^1$H-NMR (400 MHz, CDCl$_3$) δ: 0.12-0.16 (m, 2H), 0.52-0.56 (m, 2H), 0.88-0.96(m, 1H), 0.92 (s, 6H), 1.12 (s, 6H), 1.13-1.34 (m, 4H), 1.41-1.47 (m, 2H), 2.32 (d, J=6.4 Hz, 2H), 2.40-2.98 (br, 4H ), 2.94-2.96 (m, 4H), 3.58 (tt, J=12.6, 2.8 Hz, 1H), 7.05-7.18 (m, 3H), 7.22-7.24 (m, 1H).

Example 1-G

1-Cyclopropylmethyl-4-[2-(3,3,5,5-tetramethylcyclohexyl)phenyl]piperazine methanesulfonate

[Chemical Formula 12]

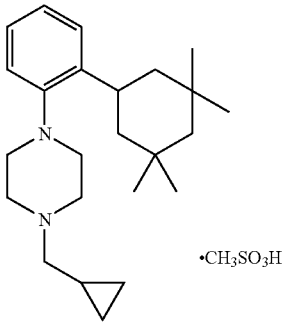

•CH$_3$SO$_3$H

A mixture of 1-cyclopropylmethyl-4-[2-(3,3,5,5-tetramethylcyclohexyl)phenyl]piperazine (277.0 g, 781.2 mmol) and methyl ethyl ketone (2493 mL) was stirred while heating at an external temperature of 81° C. Methanesulfonic acid (76.58 g, 796.8 mmol) was then added dropwise thereto over a period of 3 minutes, to form a thoroughly dissolved state. After heating and stirring for 7 minutes at an external temperature of 81° C., the external temperature was gradually lowered and stirring was continued until the internal temperature reached 37° C. The reaction suspension containing the produced precipitate was transferred to another flask using methyl ethyl ketone (100 mL). The suspension was then concentrated under reduced pressure over a period of 1 hour and 20 minutes at an external temperature of 21° C. It was then dried under reduced pressure for 30 minutes at an external temperature of 40° C. for solidification of the flask contents, to give a crude solid product of the title compound. After adding a mixed solvent of ethyl acetate (1662 mL) and heptane (1108 mL) to this crude solid product, the resulting suspension was stirred for 1 hour at an external temperature of 65° C. The suspension was then further stirred while gradually lowering the external temperature, and after the external temperature reached 45° C., stirring was continued for 14 hours at an external temperature of room temperature. The obtained suspension was filtered and the precipitated solid was collected. The solid was washed with a mixed solvent of ethyl acetate (330 mL) and heptane (220 mL) and aircured by aspiration for 4 hours at room temperature. The obtained crystals were dried for 6 hours at 70° C. in a warm-air drier to give 335.9 g of the title compound as colorless (white) powdery crystals (crystal a).

$^1$H-NMR (400 MHz, CDCl$_3$) δ: 0.47-0.51 (m, 2H), 0.81-0.85 (m, 2H), 0.94 (s, 6H), 1.10 (s, 6H), 1.15-1.43 (m, 7H), 2.85 (s, 3H), 2.95-3.11 (m, 6H), 3.43 (tt, J=12.6, 3.0 Hz, 1H), 3.52-3.61 (m, 2H), 3.80 (br d, J=11.2 Hz, 2H), 7.13-7.26 (m, 4H), 11.11 (br s, 1H).

Example 2

1-Cyclopropylmethyl-4-[2-(3,3,5,5-tetramethylcyclohexyl)phenyl]piperazine

[Chemical Formula 13]

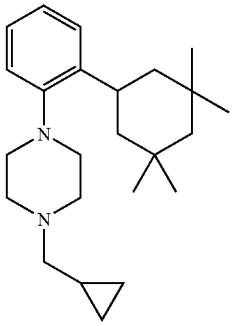

To a solution of 1-[2-(3,3,5,5-tetramethylcyclohexyl)phenyl]piperazine (200 mg, 0.666 mmol) in tetrahydrofuran (4 mL) was added cyclopropanecarbaldehyde (70 mg, 0.999 mmol), and the mixture was stirred at room temperature for 5 minutes. Sodium triacetoxyborohydride (282 mg, 1.33 mmol) was added to the reaction mixture, and after stirring for 5 minutes, acetic acid (0.038 mL, 0.666 mmol) was added and the mixture was stirred at room temperature for 2 hours.

Saturated aqueous sodium hydrogencarbonate was added to the reaction mixture and the mixture was extracted with ethyl acetate. The organic layer was dried over anhydrous sodium sulfate. The desiccant was removed by filtration and the filtrate was concentrated under reduced pressure. The resultant residue was purified by NH silica gel column chromatography (ethyl acetate/heptane) to give 182 mg of the title compound as colorless crystals (crystal A).

$^1$H-NMR (400 MHz, CDCl$_3$) δ: 0.12-0.16 (m, 2H), 0.52-0.56 (m, 2H), 0.88-0.96(m, 1H), 0.92 (s, 6H), 1.12 (s, 6H), 1.13-1.45 (m, 6H), 2.32 (d, J=6.4 Hz, 2H), 2.70 (brs, 4H), 2.95 (t, J=4.4 Hz, 4H), 3.60 (tt, J=12.4, 2.8 Hz, 1H), 7.04-7.08 (m, 1H), 7.11-7.14 (m, 2H), 7.20-7.22 (m, 1H).

Example 3

1-Cyclopropylmethyl-4-[2-(3,3,5,5-tetramethylcyclohexyl)phenyl]piperazine

[Chemical Formula 14]

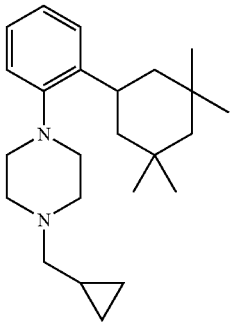

To 1-cyclopropylmethyl-4-[2-(3,3,5,5-tetramethylcyclohexyl)phenyl]piperazine (5.72 g, 16.1 mmol) was added heptane (50 mL) to form a thoroughly dissolved state, the mixture was concentrated to dryness at external temperature of 40° C. over 1 hour while adjusting reduced pressure to give 5.72 g of a colorless solid. Among the obtained colorless solid, 1.116 g (3.147 mmol) was added and suspended in a mixed solvent of ethyl alcohol (5 mL) and purified water (5 mL). The solid was triturated by sonication of the suspension for 5 minutes. Then, the mixture was allowed to stand at room temperature for 1 hour. Precipitate was collected by filtration, and aircured by aspiration for 1 hour and 30 minutes with nitrogen gas. The precipitate was dried under reduced pressure using a vacuum pump at room temperature for 4 hours, and hot-air dried at 50° C. for 4 hours to give 1.10 g of the title compound as colorless crystals (crystal B).

Example 4

1-Cyclopropylmethyl-4-[2-(3,3,5,5-tetramethylcyclohexyl)phenyl]piperazine benzenesulfonate

[Chemical Formula 15]

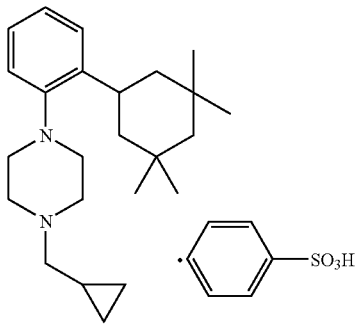

To 1-cyclopropylmethyl-4-[2-(3,3,5,5-tetramethylcyclohexyl)phenyl]piperazine (300 mg, 0.846 mmol) were added methyl alcohol (2.5 mL) and benzenesulfonic acid (136 mg, 0.863 mmol) to form a thoroughly dissolved state, followed by concentration under reduced pressure. To the obtained residual oil was added ethyl acetate to dissolve, and the mixture was allowed to stand. The suspension containing precipitated crystals was concentrated to dryness under reduced pressure. Diethyl ether was added thereto, and the solid was triturated by sonication. Precipitated crystals were collected by filtration, washed with diethyl ether, and aircured by aspiration. Drying under reduced pressure using a vacuum pump at room temperature gave 425 mg of the title compound as colorless crystals.

Example 5

1-Cyclopropylmethyl-4-[2-(3,3,5,5-tetramethylcyclohexyl)phenyl]piperazine p-toluenesulfonate

[Chemical Formula 16]

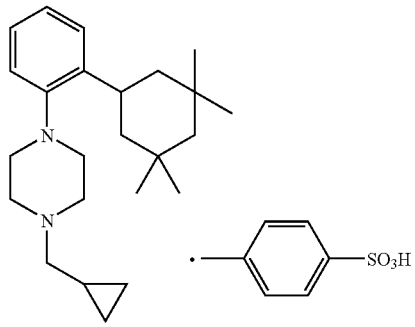

To 1-cyclopropylmethyl-4-[2-(3,3,5,5-tetramethylcyclohexyl)phenyl]piperazine (304 mg, 0.857 mmol) were added methyl alcohol (2.5 mL) and p-toluenesulfonic acid monohydrate (166 mg, 0.874 mmol) to form a thoroughly dissolved sate, and the mixture was concentrated under reduced pressure. To the obtained residual oil was added ethyl acetate to form a thoroughly dissolved state, and the mixture was allowed to stand at room temperature overnight. The suspension containing precipitated crystals was concentrated to dryness under reduced pressure. Diethyl ether was added thereto, and the solid was triturated by sonication. Precipitated crystals were collected by filtration, washed with diethyl ether, and aircured by aspiration. Drying under reduced pressure using a vacuum pump at room temperature gave 447 mg of the title compound as colorless crystals.

Example 6

1-Cyclopropylmethyl-4-[2-(3,3,5,5-tetramethylcyclohexyl)phenyl]piperazine hydrobromide

[Chemical Formula 17]

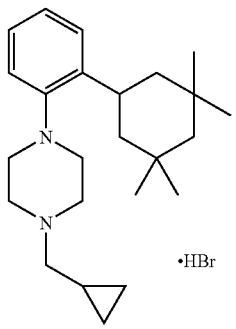

To 1-cyclopropylmethyl-4-[2-(3,3,5,5-tetramethylcyclohexyl)phenyl]piperazine (306 mg, 0.863 mmol) were added methyl alcohol (3 mL) and 47% hydrobromic acid (152 mg, 0.888 mmol) to form a thoroughly dissolved sate. Ethyl acetate was slowly added thereto at room temperature to precipitate crystals, then the suspension was concentrated to dryness under reduced pressure. A mixed solvent of diethyl ether and ethyl acetate was added thereto, and the solid was triturated by sonication. Precipitated crystals were collected by filtration, washed with diethyl ether, and aircured by aspiration. Drying under reduced pressure using a vacuum pump at room temperature gave 375 mg of the title compound as colorless crystals.

Example 7

1-Cyclopropylmethyl-4-[2-(3,3,5,5-tetramethylcyclohexyl)phenyl]piperazine sulfate

[Chemical Formula 18]

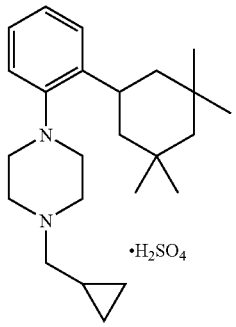

To 1-cyclopropylmethyl-4-[2-(3,3,5,5-tetramethylcyclohexyl)phenyl]piperazine (300 mg, 0.846 mmol) were added ethyl alcohol (2.5 mL), 97% sulfuric acid (85.5 mg, 0.846 mmol) and ethyl acetate to form a thoroughly dissolved sate, and the mixture was slowly concentrated to dryness while adjusting reduced pressure. Diethyl ether was added thereto, and the solid was triturated by sonication. Precipitated crystals were collected by filtration, washed with diethyl ether, and aircured by aspiration. Drying under reduced pressure using a vacuum pump at room temperature gave 368 mg of the title compound as colorless crystals (crystal a).

Example 8

1-Cyclopropylmethyl-4-[2-(3,3,5,5-tetramethylcyclohexyl)phenyl]piperazine sulfate

[Chemical Formula 19]

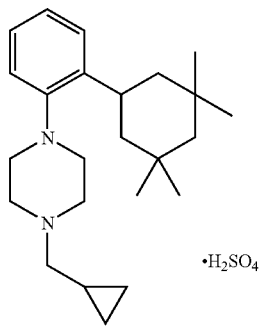

·$H_2SO_4$

To 1-cyclopropylmethyl-4-[2-(3,3,5,5-tetramethylcyclohexyl)phenyl]piperazine (310 mg, 0.874 mmol) were added ethyl alcohol (2.5 mL), 97% sulfuric acid (44.2 mg, 0.437 mmol) and ethyl acetate to form a thoroughly dissolved sate, followed by concentration under reduced pressure. To the obtained residual oil was added ethyl acetate to dissolve again, and the mixture was allowed to stand. The suspension containing precipitated crystals was concentrated to dryness under reduced pressure. A mixed solvent of diethyl ether and ethyl acetate was added to the suspension, and the solid was triturated by sonication. Precipitated crystals were collected by filtration, washed with diethyl ether, and aircured by aspiration. Drying under reduced pressure using a vacuum pump at room temperature gave 209 mg of the title compound as colorless crystals (crystal b).

Example 9

1-Cyclopropylmethyl-4-[2-(3,3,5,5-tetramethylcyclohexyl)phenyl]piperazine ethanesulfonate

[Chemical Formula 20]

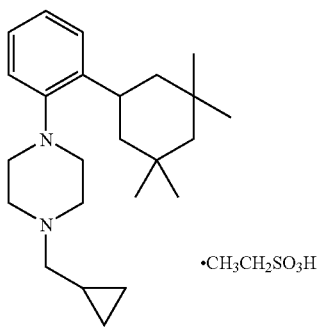

·$CH_3CH_2SO_3H$

To 1-cyclopropylmethyl-4-[2-(3,3,5,5-tetramethylcyclohexyl)phenyl]piperazine (1.30 g, 3.67 mmol) were added ethyl alcohol (1.3 mL) and ethanesulfonic acid (412 mg, 3.74 mmol), followed by heating and stirring at an external temperature of 78° C. to form a thoroughly dissolved sate. To the mixture was slowly added heptane (7 mL) over 40 minutes, then was slowly added heptane (14 mL) over 35 minutes, and the external temperature was maintained at 78° C. for 20 minutes. The suspension containing precipitated crystals was stirred for 3 hours while slowly cooling the external temperature to 35° C. The mixture was stirred at room temperature for 30 minutes, then at an external temperature of 5° C. for 1 hour. Precipitated crystals were collected by suction filtration, and aircured by aspiration over 20 minutes with nitrogen gas. The crystals were dried under reduced pressure using a vacuum pump at room temperature for 4 hours, and hot-air dried at 50° C. for 4 hours and at 60° C. for 10 hours to give 1.64 g of the title compound as colorless crystals.

Example 10

1-Cyclopropylmethyl-4-[2-(3,3,5,5-tetramethylcyclohexyl)phenyl]piperazine hydrochloride

[Chemical Formula 21]

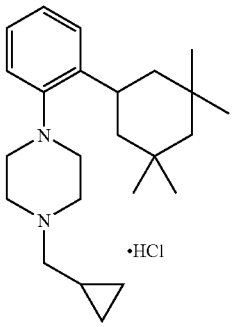

·HCl

1-Cyclopropylmethyl-4-[2-(3,3,5,5-tetramethylcyclohexyl)phenyl]piperazine (147 mg, 0.415 mmol) obtained in Example 2 was dissolve in dichloromethane (3 mL), and a 4N solution of hydrogen chloride in ethyl acetate (0.11 mL, 0.456 mmol) was added to the mixture under a nitrogen atmosphere. This was stirred at room temperature for 15 minutes, the solvent was removed under reduced pressure. To the obtained reside was added ethyl acetate (13 mL), followed by stirring at an external temperature of 100° C. for 1 hour to form a thoroughly dissolved state. Then this solution was allowed to cool down to room temperature, followed by stirring for 19 hours 45 minutes. Precipitated hydrochloride was collected by filtration to give 134 mg of the title compound as colorless crystals.

Example 11

1-Cyclopropylmethyl-4-[2-(3,3,5,5-tetramethylcyclohexyl)phenyl]piperazine hydrochloride

[Chemical Formula 22]

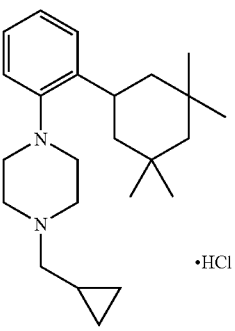

·HCl

To 1-cyclopropylmethyl-4-[2-(3,3,5,5-tetramethylcyclohexyl)phenyl]piperazine hydrochloride (99.5 mg) was added water (2.5 mL), followed by heating at 100° C. to form a dissolved state. The mixture was allowed to cool down to room temperature, and crystals were collected by filtration. The crystals were washed with heptane (0.2 mL), and dried at 60° C. for 14 hours to give 66.38 mg of the title compound as crystals (crystal II).

Example 12

1-Cyclopropylmethyl-4-[2-(3,3,5,5-tetramethylcyclohexyl)phenyl]piperazine hydrochloride

[Chemical Formula 23]

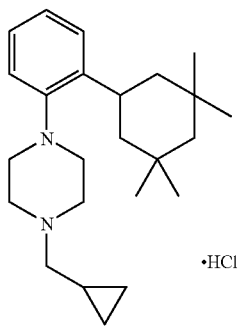

·HCl

To 1-cyclopropylmethyl-4-[2-(3,3,5,5-tetramethylcyclohexyl)phenyl]piperazine hydrochloride (100.6 mg) was added toluene (4.5 mL), followed by heating at 110° C. to form a dissolved state. The mixture was allowed to cool down to room temperature, and crystals were collected by filtration and washed with cold toluene (0.2 mL). The crystals were dried at 60° C. for 13 hours to give 90.66 mg of the title compound as crystals (crystal I).

Example 13

1-Cyclopropylmethyl-4-[2-(3,3,5,5-tetramethylcyclohexyl)phenyl]piperazine methanesulfonate

[Chemical Formula 24]

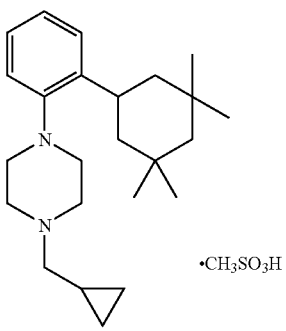

·CH₃SO₃H

1-Cyclopropylmethyl-4-[2-(3,3,5,5-tetramethylcyclohexyl)phenyl]piperazine methanesulfonate (99.93 mg) was dissolved in water (10 mL), and freeze-dried to give the title compound as crystals (crystal β).

Example 14

1-Cyclopropylmethyl-4-[2-(3,3,5,5-tetramethylcyclohexyl)phenyl]piperazine hydrochloride

[Chemical Formula 25]

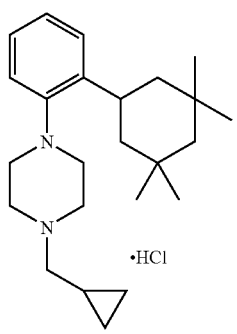

·HCl

1-Cyclopropylmethyl-4-[2-(3,3,5,5-tetramethylcyclohexyl)phenyl]piperazine hydrochloride (99.78 mg) was dissolved in water (40 mL), and freeze-dried to give the title compound as crystals (crystal III).

Example 15

1-Cyclopropylmethyl-4-[2-(3,3,5,5-tetramethylcyclohexyl)phenyl]piperazine methanesulfonate

[Chemical Formula 26]

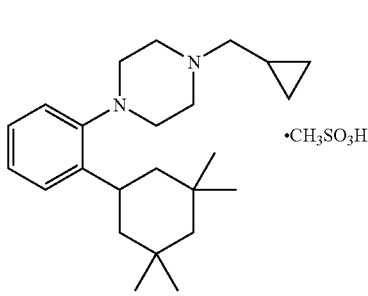

·CH₃SO₃H

Example 15-A

N-(2-Bromophenyl)formamide

[Chemical Formula 27]

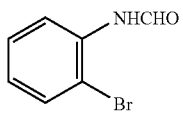

To acetic anhydride (74.2 g, 727 mmol) was added formic acid (32.9 mL, 872 mmol) under a nitrogen atmosphere while stirring at room temperature, followed by stirring at 70° C. for 3 hours. The reaction mixture was allowed to cool down to room temperature, and tetrahydrofuran (50 mL) was added.

To the solution was added a solution of 2-bromoaniline (50.0 g, 291 mmol) in tetrahydrofuran (50 mL) at room temperature, followed by stirring at the same temperature for 1 hour, and concentration was carried out. To the resultant crude crystals was added ethanol (200 mL), followed by heating and stirring at 60° C. After the crystals dissolved, the mixture was allowed to cool down to room temperature, then water (400 mL) was added, followed by stirring for 3 hours. The precipitated crystals were collected by filtration to give 48.8 g of the title compound as white crystals.

$^1$H NMR (400 MHz, CDCl$_3$) δ: 7.01 (1H, m), 7.22-37 (1.7H, m), 7.50-7.60 (0.6H, m), 7.60 (0.3H, d, J=8 Hz, NH), 7.64 (0.7H, brs, NH), 8.39 (0.7H, dd, J=1 Hz, 8 Hz), 8.49 (0.7H, s), 8.70 (0.3H, d, J=11 Hz).

Example 15-B

N-[2-(1-Hydroxy-3,3,5,5-tetramethylcyclohexyl)phenyl]formamide

[Chemical Formula 28]

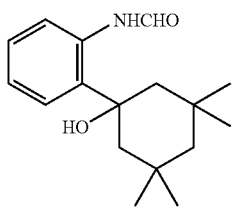

To a solution of sodium hydride (content 60%, 360 mg, 9.00 mmol) in tetrahydrofuran (5 mL) was added dropwise a solution of N-(2-bromophenyl)formamide (1.50 g, 7.50 mmol) in tetrahydrofuran (5 mL) while stirring at room temperature under a nitrogen atmosphere, followed by stirring at the same temperature for 30 minutes. The reaction mixture was cooled to −78° C., n-butyllithium (2.67 M solution in hexane, 3.37 mL, 9.00 mmol) was added dropwise thereto, followed by stirring at the same temperature for 30 minutes. To the reaction mixture was further added dropwise a solution of 3,3,5,5-tetramethylcyclohexanone (771 mg, 5.00 mmol) in tetrahydrofuran (1 mL) at the same temperature, followed by stirring at the same temperature for 1 hour and at room temperature for 1 hour. To the reaction mixture were added water (10 mL), thereafter extraction with ethyl acetate was carried out. The organic layer was washed with water and a 5% aqueous solution of sodium chloride, dried over anhydrous magnesium sulfate, filtrated, and concentrated. To the obtained crude crystals was added ethanol (7.7 mL), followed by heating and stirring at 60° C., and after the crystals were dissolved, the mixture was allowed to cool down to room temperature. Upon confirming the precipitation of crystals, water (6 mL) was added to the mixture, followed by stirring for 2 hours. The crystals were collected by filtration and dried to give 947 mg of the title compound as yellow crystals.

$^1$H NMR (400 MHz, CDCl$_3$) δ: 0.95 (6H, s), 1.17(1H, m), 1.26 (1H, s), 1.32 (6H, s), 1.50 (1H, m), 1.60 (2H, m), 2.00 (2H, m), 7.00-7.33 (3.4H, m), 8.30 (0.6H, d, J=8 Hz), 8.44 (0.6H, s), 8.63 (0.4H, d, J=12 Hz), 9.72 (0.4H, brd, J=9 Hz, NH), 10.10 (0.6H, brs, NH).

Example 15-C 2-(3,3,5,5-Tetramethylcyclohex-1-enyl)phenylamine

[Chemical Formula 29]

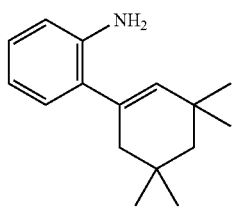

To a solution of N-[2-(1-hydroxy-3,3,5,5-tetramethylcyclohexyl)phenyl]formamide (4.00 g, 14.5 mmol) in toluene (40 mL) was added pyridinium p-toluenesulfonate (365 mg, 1.45 mmol), followed by stirring at 110° C. for 1 hour. Then, the reaction mixture was cooled down to 50° C., methanol (40 mL) and a 5N aqueous solution of sodium hydroxide (14.5 mL) were added thereto, and the reaction mixture was stirred at 80° C. for 14 hours. The reaction mixture was allowed to cool down to room temperature, the aqueous layer was removed. The organic layer was washed with water and a 5% aqueous solution of sodium chloride, dried over anhydrous magnesium sulfate, filtered, and concentrated to give 3.33 g of the title compound as a brown oil.

$^1$H NMR (400 MHz, CDCl$_3$) δ: 1.05 (6H, s), 1.09 (6H, s), 1.42 (2H, s), 2.01 (2H, s), 3.74 (2H, brs, NH$_2$), 5.51 (1H, s), 6.68 (1H, dd, J=1 Hz, 8 Hz), 6.73 (1H, dt, J=1 Hz, 8 Hz), 6.95 (1H, dd, J=1 Hz, 8 Hz), 7.03 (1H, dt, J=1 Hz, 8 Hz).

Example 15-D 2-(3,3,5,5-Tetramethylcyclohexyl)phenylamine

[Chemical Formula 30]

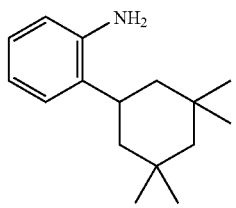

In a 100 mL autoclave, 10% palladium on carbon (water content 50%, 1.2 g) was added to a solution of 2-(3,3,5,5-tetramethylcyclohex-1-enyl)phenylamine (4.00 g, 17.4 mmol) in ethanol (40 mL), followed by stirring at room temperature, 5 kgf/cm$^2$ of hydrogen pressure for 5.5 hours. Then the reaction mixture was stirred at room temperature, 10 kgf/cm$^2$ of hydrogen pressure for 3 hours, introduction of hydrogen was stopped, and the reaction mixture was stirred at room temperature for 15 hours. The reaction mixture was stirred at room temperature, 10 kgf/cm$^2$ of hydrogen pressure for 9.5 hours, introduction of hydrogen was stopped, and the reaction mixture was stirred at room temperature for 13 hours. The reaction mixture was stirred at room temperature, 10 kgf/cm$^2$ of hydrogen pressure for 7.5 hours, and the reaction mixture was stirred at room temperature. The pressure was brought to atmospheric pressure, and the reaction mixture was filtered through Celite, and concentrated to give 3.90 g of the title compound as a brown oil.

$^1$H NMR (400 MHz, CDCl$_3$) δ: 0.95 (6H, s), 1.13 (6H, s), 1.14-1.38 (4H, m), 1.60 (2H, m), 2.86 (1H, m), 3.62 (2H, brs, NH$_2$), 6.68 (1H, dd, J=1 Hz, 8 Hz), 6.78 (1H, dt, J=1 Hz, 8 Hz), 7.02 (1H, dd, J=1 Hz, 8 Hz), 7.12 (1H, dt, J=1 Hz, 8 Hz).

Example 15-E 2-(3,3,5,5-Tetramethylcyclohexyl)phenylamine oxalate

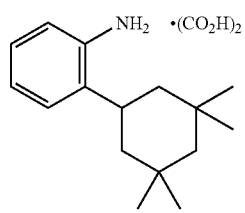

[Chemical Formula 31]

To a solution of 2-(3,3,5,5-tetramethylcyclohexyl)phenylamine (3.90 g, 16.9 mmol) in heptane (19.5 mL) was added dropwise to a solution of oxalic acid (1.82 g, 20.2 mmol) in ethyl acetate (39 mL) while stirring at room temperature, followed by stirring at the same temperature for 66 hours. Precipitated crystals were collected by glass filter, and dried to give 4.13 g of the title compound as white crystals.

$^1$H NMR (400 MHz, DMSO-d6) δ: 0.89 (6H, s), 1.10 (6H, s), 1.11 (3H, m), 1.26 (1H, m), 1.46 (2H, m), 2.87 (1H, m), 3.30 (2H, brs, NH$_2$), 6.55 (1H, t, J=8 Hz), 6.65 (1H, d, J=8 Hz), 6.87 (1H, t, J=8 Hz), 6.96 (1H, d, J=8 Hz).

Example 15-F

1-[2-(3,3,5,5-Tetramethylcyclohexyl)phenyl]piperazine methanesulfonate

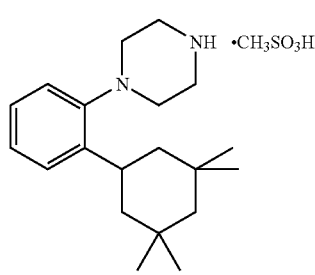

[Chemical Formual 32]

2-(3,3,5,5-Tetramethylcyclohexyl)phenylamine oxalate (4.52 g, 14.1 mmol) was suspended in t-butyl methyl ether (45 mL), and a 1N aqueous solution of potassium hydroxide (16.9 mL) was added, followed by stirring at room temperature for 50 minutes. To the reaction mixture were added t-butyl methyl ether (15 mL) and water (25 mL), and the reaction mixture was stirred at room temperature, and the organic layer was separated. The organic layer was washed with water (23 mL) four times, the solvent was removed under reduced pressure to give 3.18 g of 2-(3,3,5,5-tetramethylcyclohexyl)phenylamine as a red oil.

To a solution of 2-(3,3,5,5-tetramethylcyclohexyl)phenylamine (2.35 g, 10.2 mmol) in p-cymene (24 mL) was added bis(2-chloroethyl)amine hydrochloride (2.19 g, 12.3 mmol), followed by stirring at an external temperature of 180° C. for 8.5 hours. The reaction mixture was allowed to cool down to room temperature, diluted with addition of p-cymene (4 mL), and divided into three portions. To one portion of the reaction mixture was added a 1N aqueous solution of sodium hydroxide (7.8 mL), and the mixture was stirred at room temperature, and the organic layer was separated. The organic layer was washed with water (8 mL) and a 5% aqueous solution of sodium chloride in this order, and diluted with addition of ethyl acetate (9 mL). To the mixture was added methanesulfonic acid (0.19 mL, 2.93 mmol), followed by stirring at room temperature for 1 hour. Produced precipitate was collected by filtration under reduced pressure, washed with ethyl acetate (8 mL), dried at 40° C. under reduced pressure for 1 hour to give 974 mg of crude crystals of the title compound as a light brown solid.

The crude crystals of the title compound (500 mg, content 90.2%, 1.14 mmol) was suspended in toluene (4.5 mL), followed by heating and stirring at 100° C. to completely dissolve the crystals. To the mixture was added heptane (2.3 mL), and heating was stopped and stirring was carried out. After crystals were precipitated, the mixture was stirred at room temperature for 5.5 hours. Produced precipitate was collected by filtration under reduced pressure, washed with a mixed solvent of toluene (2.25 mL) and heptane (2.25 mL), and dried at 40° C. under reduced pressure to give 413 mg of the title compound as a light brown solid.

$^1$H-NMR (400 MHz, CDCl$_3$) δ: 0.93 (s, 6H), 1.11 (s, 6H), 1.14-1.42 (m, 6H), 2.85 (s, 3H), 3.17 (brs, 4H), 3.39 (brs, 4H), 3.47 (tt, J=13, 3 Hz, 1H), 7.12-7.18 (m, 3H), 7.25-7.26 (m, 1H).

Example 15-G

1-Cyclopropylmethyl-4-[2-(3,3,5,5-tetramethylcyclohexyl)phenyl]piperazine methanesulfonate

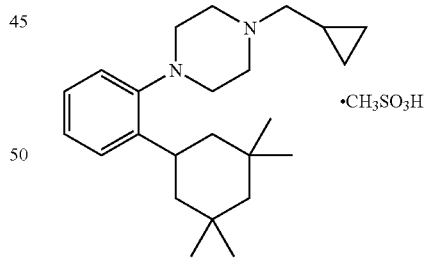

[Chemical Formula 33]

1-[2-(3,3,5,5-Tetramethylcyclohexyl)phenyl]piperazine methanesulfonate (820 mg, 2.07 mmol) was suspended in t-butyl methyl ether (8.2 mL), and a 1N aqueous solution of sodium hydroxide (2.5 mL) was added thereto, followed by stirring at room temperature for 40 minutes. The organic layer was separated and washed twice with water (8 mL), and the solvent was removed under reduced pressure. To the resultant residue were added tetrahydrofuran (6.1 mL), acetic acid (0.116 mL) and cyclopropanecarbaldehyde (0.182 mL) in this order, followed by stirring at room temperature for 20 minutes. To the mixture was added sodium triacetoxyborohydride (606 mg, 2.86 mmol), followed by stirring at room temperature for 1.5 hours. To the reaction mixture were added a 1N aqueous solution of sodium hydroxide (8.1 mL) and t-butyl methyl ether (6.1 mL), followed by stirring at room temperature, and the organic layer was separated. The organic layer was washed twice with water (6 mL), and the solvent was removed under reduced pressure. To the resultant residue was added 4-methyl-2-pentanone (6 mL), followed by heating and stirring at an external temperature of 100° C. Methanesulfonic acid (0.121 mL, 1.86 mmol) was added thereto and dissolved. The mixture was further stirred at an external temperature of 100° C. for 2 minutes, heptane (3 mL) was added, and heating was stopped and stirring was carried out. The mixture was stirred at room temperature for 14 hours and the produced precipitate was collected by filtration under reduced pressure. The precipitate was washed with a mixture of 4-methyl-2-pentanone (3 mL) and heptane (3 mL), and dried under reduced pressure at 40° C. for 2 hour to give 670 mg of the title compound as white crystals (crystal α).

NMR data and Powder X-ray diffraction data for the product corresponded with that for the compound obtained in Example 1-G (FIG. 1 and Table 1).

Example 16

1-Cyclopropylmethyl-4-[2-(3,3,5,5-tetramethylcyclohexyl)phenyl]piperazine methanesulfonate Example 16-A 1-Cyclopropylmethyl-4-[2-(3,3,5,5-tetramethylcyclohexyl)phenyl]piperazine To N-methyl-2-pyrrolidinone (NMP) (1800 mL) was added 1-[2-(3,3,5,5-tetramethylcyclohexyl)phenyl]piperazine methanesulfonate (217.1 g) while stirring under nitrogen stream. At the same time washing with N-methyl-2-pyrrolidinone (20 mL) was carried out. The mixture was stirred at 42° C. (external temperature) for 1 hour 40 minutes, and cyclopropanecarbaldehyde (42.4 g) was added to prepare a solution of iminium salt.

On the other hand, a mixture of $NaBH_4$ (28.7 g) and tetrahydrofuran (1000 mL) was stirred at 7° C. (external temperature) under nitrogen stream. To the mixture was added dropwise acetic acid (156.8 g) at 15° C. or below (internal temperature) over 30 minutes, followed by stirring at the same temperature for 1 hour. To the mixture was added dropwise the solution of iminium salt above over 35 minutes, and washing with N-methyl-2-pyrrolidinone (180 mL) was carried out.

Upon completion of the dropwise addition, the mixture was stirred at 15° C. or below (internal temperature) for 1 hour 54 minutes, and water (100 mL) was added dropwise over 8 minutes. To the mixture was added methyl t-butyl ether (MTBE) (100 mL) over 1 minute, and a 5N aqueous solution of sodium hydroxide (500 mL) was added dropwise over 3 minutes.

To the mixture was added methyl t-butyl ether (50 mL), and the organic layer was washed twice with water (1000 mL) and once with water for injection (1000 mL). The organic layer was concentrated under reduced pressure using an evaporator to approximately 400 mL. To the mixture was added ethyl acetate (400 mL), followed by concentration under reduced pressure (at 50° C.) to approximately 400 mL, and ethyl acetate (400 mL) was added again, followed by concentration under reduced pressure (at 50° C.) to approximately 400 mL.

To the mixture was added ethyl acetate (400 mL), followed by stirring at room temperature for 14 minutes and heating at 50° C. (external temperature). The mixture was concentrated under reduced pressure (at 50° C.) to 400 mL, and ethyl acetate (200 mL) was added, followed by heating at 50° C. (external temperature) to give an ethyl acetate solution (608.7 g) containing 1-cyclopropylmethyl-4-[2-(3,3,5,5-tetramethylcyclohexyl)phenyl]piperazine.

Example 16-B

1-Cyclopropylmethyl-4-[2-(3,3,5,5-tetramethylcyclohexyl)phenyl]piperazine methanesulfonate

[Chemical Formula 34]

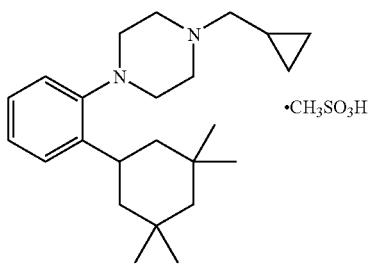

·$CH_3SO_3H$

The ethyl acetate solution (608.7 g) containing 1-cyclopropylmethyl-4-[2-(3,3,5,5-tetramethylcyclohexyl)phenyl]piperazine synthesized in Example 16-A above was filtered through a filter paper under slightly reduced pressure. To the mixture was added ethyl acetate (150 mL) through the filter paper, followed by heating and stirring at 40° C. (external temperature). To the mixture was added dropwise methanesulfonic acid (32.4 mL) over 6 minutes. To the mixture was added heptane (1290 mL) over 3 minutes, and the mixture was stirred at 40° C. (external temperature) for 1 hour and 10 minutes, then at 30° C. (external temperature) for 27 minutes. The mixture was stirred at 20° C. (external temperature) for 37 minutes, then at 7° C. (external temperature) overnight (22 hours).

Precipitated crystals were collected by filtration using a filter paper, and the crystals were washed with a mixed solvent of ethyl acetate (160 mL) and heptane (320 mL). The crystals were dried under reduced pressure using a evaporator (at 40° C.) for 3 hours to give 1-cyclopropylmethyl-4-[2-(3,3,5,5-tetramethylcyclohexyl)phenyl]piperazine methanesulfonate (209.5 g) as white crystals (crystalα).

NMR data and Powder X-ray diffraction data for the product corresponded with that for the compound obtained in Example 1-G (FIG. 1 and Table 1).

(Measurement of Powder X-ray Diffraction Pattern)

The powder X-ray diffraction patterns for the respective Examples were measured using the apparatus below and under conditions below. The measured patterns were shown in FIGS. 1 to 13.

(Apparatus)

Rigaku X-ray DTA system: RINT-2000 manufactured by Rigaku Corporation (Operation Method)

Samples were ground in a mortar and then sampled on a 5 or 10-mm diameter glass plate. Measurement was carried out under the conditions below.

(Conditions)

X-ray in use: CuKα ray

Tube voltage: 40 kV

Tube current: 200 mA

Divergent slit: ½ deg

Receiving slit: 0.3 mm

Scattering slit: ½ deg

Scanning speed: 2° or 5°/min

Scanning step: 0.02°

Scanning range (2θ): 5 to 40°

Table 1 shows the peaks and their intensities at diffraction angles (2θ) for the crystals of methanesulfonate obtained in Example 1-G.

TABLE 1

| Peak # | 2 θ | Half width | d-value | Intensity | Relative intensity |
|---|---|---|---|---|---|
| 1 | 7.000 | 0.141 | 12.6175 | 62218 | 100 |
| 2 | 11.960 | 0.165 | 7.3937 | 2245 | 4 |
| 3 | 12.620 | 0.165 | 7.0084 | 1495 | 2 |
| 4 | 13.100 | 0.188 | 6.7527 | 9357 | 15 |
| 5 | 15.380 | 0.165 | 5.7564 | 12360 | 20 |
| 6 | 16.420 | 0.118 | 5.3941 | 897 | 1 |
| 7 | 16.800 | 0.165 | 5.2729 | 2342 | 4 |
| 8 | 17.060 | 0.165 | 5.1931 | 2827 | 5 |
| 9 | 17.640 | 0.188 | 5.0237 | 3468 | 6 |
| 10 | 18.340 | 0.188 | 4.8335 | 28213 | 45 |
| 11 | 18.880 | 0.165 | 4.6964 | 3208 | 5 |
| 12 | 19.460 | 0.188 | 4.5577 | 9917 | 16 |
| 13 | 19.940 | 0.212 | 4.4491 | 6580 | 11 |
| 14 | 20.680 | 0.188 | 4.2915 | 9282 | 15 |
| 15 | 21.100 | 0.188 | 4.2070 | 2795 | 4 |
| 16 | 22.000 | 0.212 | 4.0369 | 4805 | 8 |
| 17 | 23.060 | 0.212 | 3.8537 | 5908 | 9 |
| 18 | 23.240 | 0.118 | 3.8243 | 4340 | 7 |
| 19 | 23.860 | 0.212 | 3.7263 | 3563 | 6 |
| 20 | 24.360 | 0.188 | 3.6509 | 1502 | 2 |
| 21 | 25.020 | 0.141 | 3.5561 | 2570 | 4 |
| 22 | 25.380 | 0.188 | 3.5064 | 1507 | 2 |
| 23 | 25.780 | 0.141 | 3.4529 | 1103 | 2 |
| 24 | 26.660 | 0.188 | 3.3409 | 4223 | 7 |
| 25 | 26.860 | 0.141 | 3.3165 | 3382 | 5 |
| 26 | 27.600 | 0.188 | 3.2292 | 1635 | 3 |
| 27 | 28.420 | 0.259 | 3.1379 | 2073 | 3 |
| 28 | 29.320 | 0.141 | 3.0436 | 1660 | 3 |
| 29 | 29.900 | 0.188 | 2.9859 | 2565 | 4 |
| 30 | 30.740 | 0.212 | 2.9062 | 1637 | 3 |
| 31 | 31.920 | 0.212 | 2.8014 | 1672 | 3 |
| 32 | 32.620 | 0.212 | 2.7428 | 1158 | 2 |
| 33 | 35.280 | 0.188 | 2.5419 | 1115 | 2 |
| 34 | 35.700 | 0.212 | 2.5129 | 1322 | 2 |
| 35 | 36.900 | 0.165 | 2.4339 | 1328 | 2 |
| 36 | 37.380 | 0.282 | 2.4038 | 1035 | 2 |

Table 2 shows the major peaks at diffraction angles (2θ) for the crystals obtained in Examples 9 and 11 to 14.

TABLE 2

| | Example | | | | |
|---|---|---|---|---|---|
| | 9 | 11 | 12 | 13 | 14 |
| Major Peaks (2θ) | 6.8 | 12.6 | 5.6 | 13.9 | 8.7 |
| | 13.0 | 14.7 | 10.1 | 16.0 | 14.3 |
| | 15.3 | 15.7 | 11.2 | 19.6 | 17.4 |
| | 17.5 | 17.1 | 13.7 | 23.1 | 19.1 |
| | 19.3 | | 14.6 | | |
| | 20.5 | | 15.7 | | |
| | | | 16.1 | | |
| | | | 17.1 | | |
| | | | 17.8 | | |

(Measurement of $^{13}$C Solid State NMR Spectrum)

$^{13}$C Solid State NMR spectrum was measured for the crystals of methanesulfonate obtained in Example 1-G under the conditions below.

Apparatus: AVANCE 400 MHz (Bruker, Switzerland)
Probe: 7 m m-CP/MAS (Bruker)
NMR cell diameter: 7 mm
Measurement temperature: room temperature (~22° C.)
Measurement nucleus: $^{13}$C (100.6248425 MHz)
Pulse mode: CP/TOSS measurement
Frequency: 6000 Hz
Accumulation: 512
Waiting time: 10 sec
Contact time: 5000 μsec
External standard: chemical shift of carbonyl carbon of glycine was set as 176.03 ppm.

Figure 14:
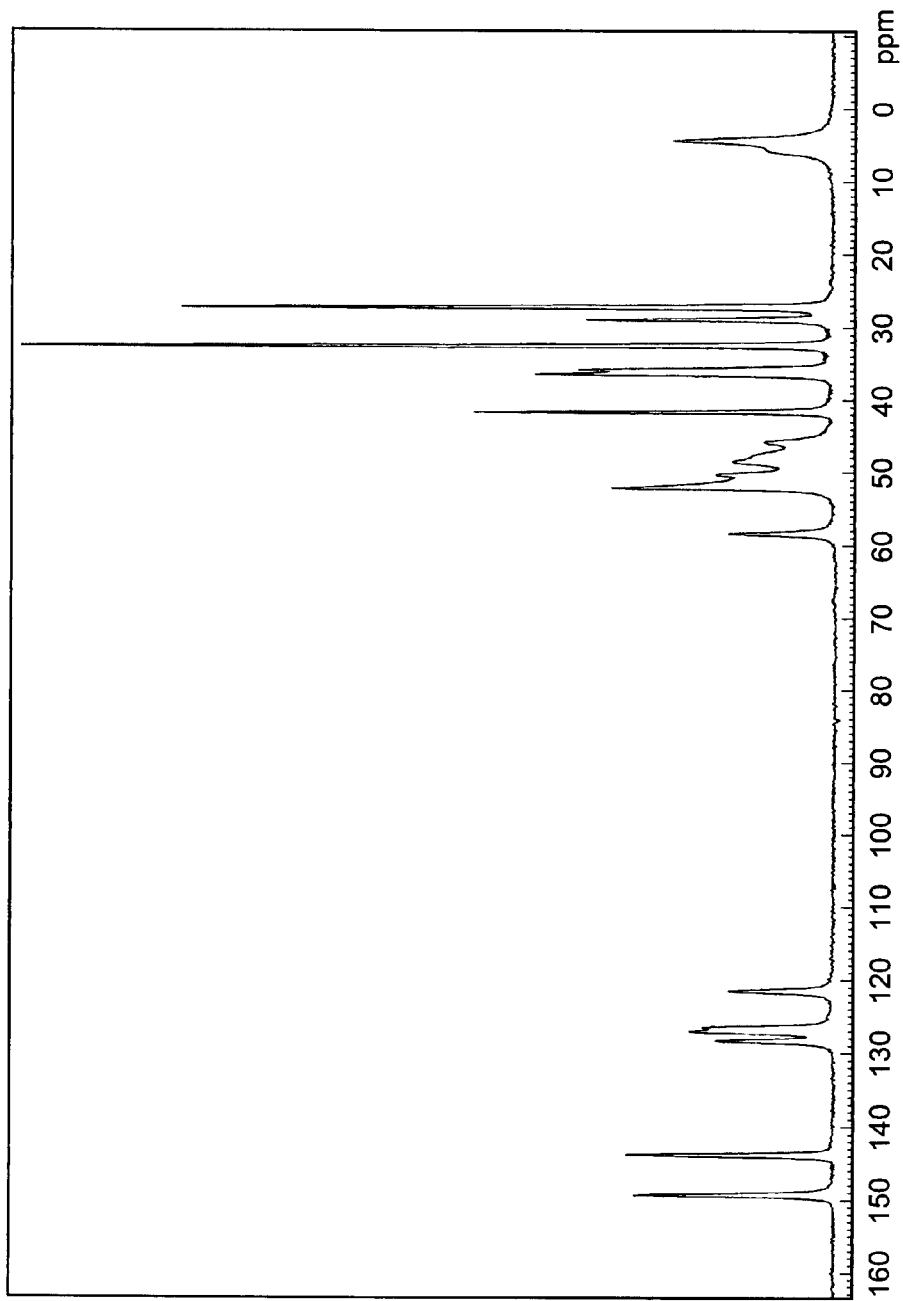
FIG. 14 shows a $^{13}$C Solid State Nuclear Magnetic Resonance (NMR) spectrum of the crystal of 1-cyclopropylmethyl-4-[2-(3,3,5,5-tetramethylcyclohexyl)phenyl]piperazine methanesulfonate (crystal α) obtained in Example 1-G.

FIG. 14 shows a $^{13}$C Solid State NMR spectrum of the crystals of methanesulfonate obtained in Example 1-G, and the chemical shifts are summarized in Table 3.

TABLE 3

| Chemical Shift (ppm) |
|---|
| 4.3 |
| 27.1 |
| 28.9 |
| 32.5 |
| 36.4 |
| 41.6 |
| 52.0 |
| 58.4 |
| 121.5 |
| 127.0 |
| 128.3 |
| 143.8 |
| 149.3 |

(Evaluation of Compounds)

1-Cyclopropylmethyl-4-[2-(3,3,5,5-tetramethylcyclohexyl)phenyl]piperazine hydrochloride obtained in Example 10 or by the method similar to Example 10 (hereinafter refereed to as the hydrochloride of Example 10) was evaluated according to the Test Example 1 to 4 below.

Test Example 1

Evaluation of Compounds in Jurkat Cell Adhesion System

<Immobilization of Human Fibronectin in 96-well Plate>

Human fibronectin (Becton Dickinson Biosciences) was diluted with phosphate-buffered saline (hereinafter abbreviated as PBS; Sigma) to 0.1-0.01 g/mL, and the diluted solution was added to a 96-well plate (Becton Dickinson) at 50 μL/well, and allowed to stand overnight at 4° C. On the following day, the supernatant was removed from the plate, and then PBS containing 1% bovine serum albumin (hereinafter abbreviated as BSA; Sigma) was added thereto at 100 μL/well and incubation was performed at 37° C. for 2 hours in a $CO_2$ incubator (Hirasawa).

<Adhesion Assay>

The supernatant was removed from each plate and Jurkat cells suspended in RPMI-1640 (Sigma) containing 1 mg/mL BSA were added at 80 μL/well for 2.5×10⁵ cells/well. The compound diluted to different concentrations with RPMI-1640 containing 1 mg/mL BSA was immediately added at 10 μL/well, and then 100 nM phorbol myristate acetate (hereinafter abbreviated as PMA; Sigma) in RPMI-1640 containing 1 mg/mL BSA was added at 10 μL/well and the plate was incubated in a $CO_2$ incubator at 37° C. for 45-60 minutes. The supernatant was removed from the plate and each well was washed several times with 100 μL/well of RPMI-1640, after which 50 mM citrate buffer (pH 5.0) containing 3.75 mM p-nitrophenol-N-acetyl-α-D-glucosaminide (Sigma) and 0.25% Triton X-100 (Sigma) were added at 60 μL/well, and the mixture was placed in a $CO_2$ incubator and incubated at 37° C. for 45 minutes. After incubation, 50 mM glycine buffer (pH 10.4) containing 5 mM EDTA was added at 90 μL/well, and the absorbance at 405 nm was measured with an EL340 Automated Microplate Reader (BIO-TEK) to determine the adhered cell count. With regard to IC50 (concentration which inhibited the increase in the number of adhered cells by the PMA-stimulation by 50%), that for 1-cyclopropylmethyl-4-[2-(3,3,5,5-tetramethylcyclohexyl)phenyl]piperazine hydrochloride (hydrochloride of Example 10) is 3.1 μM, and that for 1-cyclopropylmethyl-4-[2-(3,3,5,5-tetramethylcyclohexyl)phenyl]piperazine methanesulfonate (crystal α) is 4.7 μM.

Test Example 2

Evaluation of Compounds in Human Peripheral Blood Neutrophil Adhesion System

<Preparation of Human Peripheral Blood Neutrophils>

To a plastic centrifugation tube containing 100 units of heparin sodium (Shimizu Pharmaceutical) was added 25 mL of fresh blood sampled from a healthy human. After adding and mixing therewith 8 mL of physiological saline (Otsuka Pharmaceutical) containing 6% Dextran (Nacalai), the mixture was allowed to stand at room temperature for 45 minutes for sedimentation of the erythrocytes. The resultant supernatant was transferred to another plastic centrifugation tube and combined with an equivalent volume of PBS, and then centrifuged at 1600 rpm for 7 minutes at room temperature. The obtained hematocyte fraction was suspended in 4 mL of PBS, and the suspension was superposed on 4 mL of Ficoll-Paque™ PLUS (Amersham Biosciences). The resultant bilayer liquid was centrifuged at 2000 rpm for 30 minutes at room temperature, after which the supernatant was removed and the precipitate was suspended in 10 mL of PBS and centrifuged at 1200 rpm for 7 minutes, and the supernatant was removed. The resulting precipitate was suspended in 0.5 mL of PBS again, and then 10 mL of distilled water (Otsuka Pharmaceutical) was added, 0.5 mL of an aqueous solution containing 3 M NaCl was immediately added to restore isotonicity, the mixture was centrifuged at 1200 rpm for 7 minutes, and the obtained precipitate was suspended in PBS containing 1 mg/mL BSA again and stored in ice until being used for the experiment.

<Fluorescent Labeling of Human Peripheral Blood Neutrophils>

The obtained neutrophils were suspended in PBS containing 1 mg/mL BSA at $2 \times 10^7$ cells/mL. BCECF-AM (Dojin) was added to a final concentration of 5 μM, and the mixture was incubated at 37° C. for 45 minutes. It was then rinsed twice with PBS containing 1 mg/mL BSA by centrifugation, suspended again in PBS containing 1 mg/mL BSA at $5 \times 10^7$ cells/mL, and stored in ice until use.

<Preparation of HUVEC Immobilized Plate>

Human umbilical vein endothelial cells (hereinafter abbreviated as HUVEC) were suspended in MCDB131 medium (Chlorella Industries) containing 10% fetal calf serum and 30 μg/mL endothelial cell growth supplement (Becton Dickinson Bioscience). The suspension was added at $7.5 \times 10^3$ cells/well to a 96-well plate (Iwaki) immobilized with type I collagen, and cultured for 3 days in a $CO_2$ incubator (Hirasawa). Upon confirming confluency of the cells, the supernatant was discarded, the plate was rinsed twice with PBS, and then PBS containing 0.1% glutaraldehyde (Kanto Kagaku) was added at 100 μL/well and the HUVECs were immobilized for 5 minutes. The supernatant was discarded and the plate was washed twice with PBS, and then PBS was added at 100 μL/well and the mixture was stored at 4° C. until use.

<Adhesion Assay>

To 6.5 mL of RPMI-1640 medium (Sigma) containing 1 mg/mL of BSA were added 0.5 mL of a suspension of BCECF-AM labeled neutrophils at $5 \times 10^7$/mL stored in ice, which was mixed, and the mixture was added at 80 μL/well to a HUVEC immobilized plate. To this plate were immediately added 10 μL/well of a solution of the compound diluted at different concentrations with RPMI-1640 containing 1 mg/mL BSA, and 10 μL/well of 100 nM PMA in RPMI-1640 containing 1 mg/mL BSA, and the mixture was incubated in a $CO_2$ incubator at 37° C. for 45 minutes. The supernatant was removed from the plate, which was then washed several times with RPMI-1640 at 100 μL/well, and then PBS containing 0.1% NP-40 (Calbiochem) was added thereto at 100 μL/well and the fluorescent intensity was measured with an ARVO™SX 1420 multi label counter (Wallac) to determine the number of adhered cells. With regard to IC50 (concentration which inhibited the increase in the number of adhered cells by the PMA-stimulation by 50%), that for 1-cyclopropylmethyl-4-[2-(3,3,5,5-tetramethylcyclohexyl)phenyl]piperazine hydrochloride (hydrochloride of Example 10) is 6.7 μM, and that for 1-cyclopropylmethyl-4-[2-(3,3,5,5-tetramethylcyclohexyl)phenyl]piperazine methanesulfonate (crystal α) is 7.1 μM.

Test Example 3

Evaluation of Compounds in Oxazolone-Induced Colon Neutrophil Infiltration Model <Sensitization with Oxazolone>

Five- to six-week-old male Balb/c mice (Charles River Japan) were shaven at the abdomen to an approximately 2 cm square area. A 100% ethanol solution containing 3% 4-ethoxymethylene-2-phenyl-2-oxazolin-5-one (hereinafter referred to as "oxazolone"; Sigma) was applied at 150 μl onto the abdomen of each mouse.

<Preparation of Emulsion Containing Oxazolone>

Distilled water (Otsuka Pharmaceutical) was added in an equivalent volume to 100% peanut oil (Kanto Kagaku) containing 1% oxazolone, and the components were vigorously mixed with a glass syringe (Top Co.), to prepare an emulsion containing 0.5% oxazolone.

<Induction with Oxazolone>

The mice were fasted on the 3rd day after oxazolone sensitization, and were injected with 100 μl of the emulsion containing 0.5% oxazolone prepared in the way described above intrarectally at a site approximately 3 cm from the anus under ether anesthesia on the 4th day.

<Colon-infiltrating Neutrophil Assay>

Each compound was suspended or dissolved in an aqueous solution containing 0.5% methyl cellulose (Wako), and orally administered at 30 mg/kg 30 minutes prior to the intrarectal injection of oxazolone emulsion. Four hours after the intrarectal injection of oxazolone, mice were sacrificed by cervical dislocation, and colons were extirpated, dissected in the longitudinal direction, washed with physiological saline, and transferred to ice-cooled plastic centrifugation tubes.

After adding 1 mL of 50 mM potassium phosphate buffer (hereinafter abbreviated as KPB) (pH 6.0) to the tube, and the tissue were homogenized with PHYSCOTRON (Microtec Nition Co., Ltd.), 2 mL of 50 mM KPB (pH 6.0) was added and the mixture was centrifuged at 3000 rpm, 4° C. for 10 minutes and the supernatant was removed. To the resultant precipitate was added 1 mL of 50 mM KPB (pH 6.0) containing 0.5% hexadecyltrimethyl-ammonium bromide (Sigma), and freeze-thawed 3 to 5 times using liquid nitrogen and hot water, centrifuged at 3000 rpm, 4° C. for 10 minutes to yield a supernatant. The myeloperoxidase enzyme activity in the supernatant was assayed in the following manner. Specifically, to 10 µL of the obtained supernatant was added 200 µL of 50 mM KPB (pH6.0) containing 0.017% o-dianisidine (Sigma) and 0.0005% hydrogen peroxide (Wako), incubated at 37° C., and the change in absorbance at 450 nm (the rate of change in absorbance per minute (mO.D./min.)) was continuously measured for 1 minute using an EL340 Automated Microplate Reader (BIO-TEK) in kinetic mode. Myeloperoxidase enzyme inhibitory rate (%) in each compound administered group with respect to the oxazolone control group (the oxazolone emulsion intrarectally injected/compound-free group), was 35%.

Test Example 4

Evaluation of Compounds in DSS-Induced Colitis Model

A 1-3% solution of dextran sulfate sodium (hereinafter abbreviated as DSS; ICN) in purified water was fed freely to 6- to 7-week-old male Balb/c mice for 5-7 days to induce colitis. Disease Activity Index (hereinafter abbreviated as DAI) scored based on fecal hardness, blood content in feces and body weight change, the number of neutrophils infiltrating the colon and the length of the colon were used as indexes to evaluate compounds. Each compound was suspended or dissolved in an aqueous solution containing 0.5% methyl cellulose (Wako), and orally administered at 30 mg/kg once a day, for 5-7 successive days. Hydrochloride of Example 10 administered group exhibited particularly good improvement in comparison with the DSS control group, i.e. the DSS water-loaded/compound-free group.

INDUSTRIAL APPLICABILITY

The compounds of the invention have excellent cell adhesion inhibitory action and cell infiltration inhibitory action, and therefore may be medicaments useful as therapeutic or prophylactic agents for various inflammatory diseases and autoimmune diseases associated with adhesion and infiltration of leukocytes, such as inflammatory bowel disease (particularly ulcerative colitis or Crohn's disease), irritable bowel syndrome, rheumatoid arthritis, psoriasis, multiple sclerosis, asthma or atopic dermatitis.

The invention claimed is:

1. An acid salt of 1-cyclopropylmethyl-4-[2-(3,3,5,5-tetramethylcyclohexyl)phenyl]piperazine or hydrate thereof, wherein the acid is selected from the group consisting of methanesulfonic acid, hydrochloric acid, ethanesulfonic acid, benzenesulfonic acid, p-toluenesulfonic acid, hydrobromic acid and sulfuric acid.

2. 1-Cyclopropylmethyl-4-[2-(3,3,5,5-tetramethylcyclohexyl)phenyl]piperazine methanesulfonate or hydrate thereof.

3. 1-Cyclopropylmethyl-4-[2-(3,3,5,5-tetramethylcyclohexyl)phenyl]piperazine hydrochloride or hydrate thereof.

4. 1-Cyclopropylmethyl-4-[2-(3,3,5,5-tetramethylcyclohexyl)phenyl]piperazine ethanesulfonate or hydrate thereof.

5. 1-Cyclopropylmethyl-4-[2-(3,3,5,5-tetramethylcyclohexyl)phenyl]piperazine benzenesulfonate or hydrate thereof.

6. 1-Cyclopropylmethyl-4-[2-(3,3,5,5-tetramethylcyclohexyl)phenyl]piperazine p-toluenesulfonate or hydrate thereof.

7. 1-Cyclopropylmethyl-4-[2-(3,3,5,5-tetramethylcyclohexyl)phenyl]piperazine hydrobromide or hydrate thereof.

8. 1-Cyclopropylmethyl-4-[2-(3,3,5,5-tetramethylcyclohexyl)phenyl]piperazine sulfate or hydrate thereof.

9. A crystal of 1-cyclopropylmethyl-4-[2-(3,3,5,5-tetramethylcyclohexyl)phenyl]piperazine methanesulfonate having a diffraction peak at a diffraction angle ($2\theta \pm 0.2°$) of 7.0° in a powder X-ray diffraction.

10. The crystal according to claim 9 further having a diffraction peak at a diffraction angle ($2\theta \pm 0.2°$) of 18.3° in a powder X-ray diffraction.

11. The crystal according to claim 10 further having diffraction peaks at diffraction angles ($2\theta \pm 0.2°$) of 13.1° and 15.4° in a powder X-ray diffraction.

12. A crystal of 1-cyclopropylmethyl-4-[2-(3,3,5,5-tetramethylcyclohexyl)phenyl]piperazine methanesulfonate having peaks at chemical shifts of around 4.3 ppm and around 149.3 ppm in a $^{13}C$ Solid State Nuclear Magnetic Resonance spectrum.

13. The crystal according to claim 12 further having peaks at chemical shifts of around 121.5 ppm and around 143.8 ppm in a $^{13}C$ Solid State Nuclear Magnetic Resonance spectrum.

* * * * *